United States Patent [19]
Lehrer

[11] Patent Number: 5,685,856
[45] Date of Patent: Nov. 11, 1997

[54] COAXIAL BLUNT DILATOR AND ENDOSCOPIC CANNULA INSERTION SYSTEM

[76] Inventor: Theodor Lehrer, 936 Intracoastal Dr,. Apt. 21C, Ft. Lauderdale, Fla. 33304

[21] Appl. No.: 607,862

[22] Filed: Feb. 27, 1996

[51] Int. Cl.$^6$ ............................................. A61M 5/18
[52] U.S. Cl. ............................................. 604/170; 604/164
[58] Field of Search ............................ 604/164, 165, 604/166, 167, 170, 158

[56] References Cited

U.S. PATENT DOCUMENTS

| | | | |
|---|---|---|---|
| 2,705,949 | 8/1955 | Silverman | 604/165 |
| 5,232,442 | 8/1993 | Johnson | 604/164 |
| 5,250,036 | 10/1993 | Farivar | 604/165 |
| 5,273,545 | 12/1993 | Hunt | 604/167 |
| 5,370,623 | 12/1994 | Kreamer | 604/165 |

*Primary Examiner*—Sam Rimell
*Assistant Examiner*—Luke J. Yeh
*Attorney, Agent, or Firm*—John C. Smith

[57] ABSTRACT

A coaxial blunt dilator insertion system for insertion of laparoscopic cannulas which uses a coaxial needle guide and blunt dilator instead of a sharp trocar to insert primary and secondary laparoscopic cannulas. A single blunt dilator allows the insertion path to be expanded from the diameter of a needle to a size capable of accepting a digital cannula. Alternative embodiments allow multiple dilators to be used in sequence to expand the opening in the body cavity for a larger sized cannula. The size of the insertion path can thus accommodate both narrow devices such as suture graspers and optical devices up to and including objects as large as a surgeons finger. Open laparoscopy insertion of the first cannula may be performed under improved visual guidance utilizing a Laparoscopic Optically Directed Insertion System ("LODIS"). A blunt optical sleeve guide of appropriate length is fitted over the micro laparoscope and bluntly opens the peritoneum. The sleeve guide is backloaded with a blunt dilator and a laparoscopic cannula. Alternatively, the micro laparoscope may be used to visually control a sharpened double action grasper to enter the peritoneal cavity. When using a primary closed laparoscopy technique, the micro laparoscope allows verification of the correct position of the needle and the outer sleeve prior to creating the pneumoperitoneum, thus enhancing safety.

11 Claims, 20 Drawing Sheets

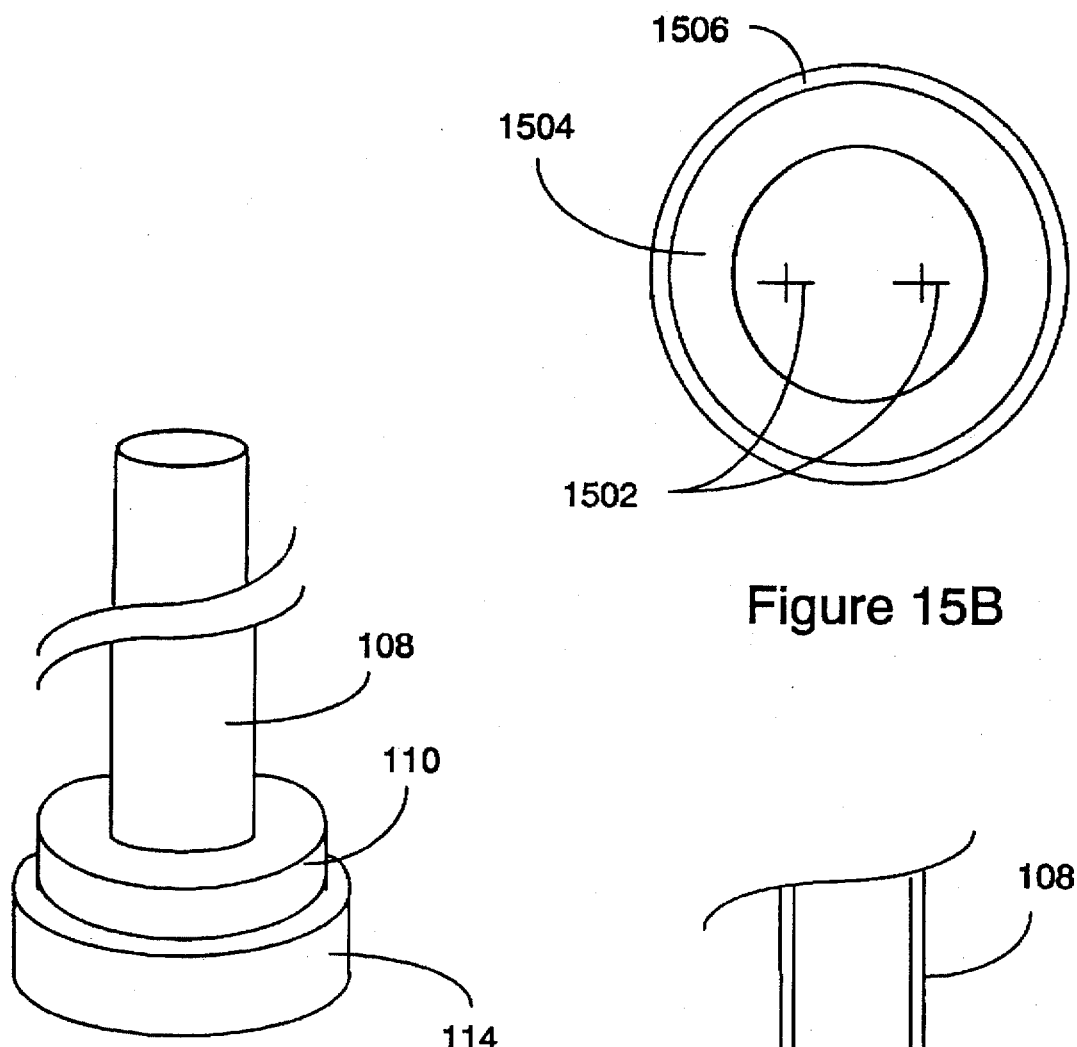
Figure 15B
Figure 15A
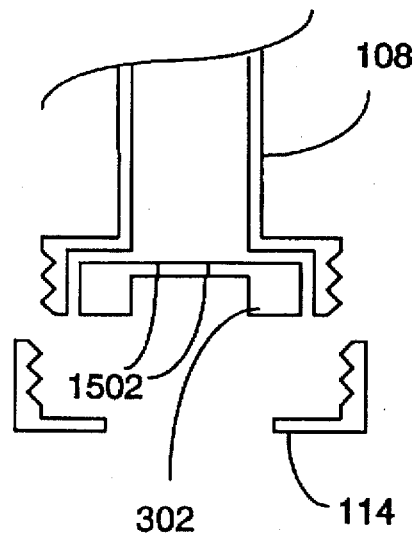
Figure 15C

COAXIAL BLUNT DILATOR AND ENDOSCOPIC CANNULA INSERTION SYSTEM

BACKGROUND OF THE INVENTION

1. Technical Field

The present invention relates to laparoscopic surgical instruments. In particular, it relates to a coaxial insufflation needle, outer sleeve and blunt dilator which replaces sharp trocars to insert primary and secondary laparoscopic cannulas. This non-trocar insertion system comprises an insufflation needle which has a blunt spring-loaded central or inner shaft extending past its sharp distal end; a blunt outer sleeve guide; an optical outer sleeve guide; and a variety of laparoscopic cannulas (2 mm, 5 mm, 7 mm, 10 mm, 12 mm) and a digital cannula.

2. Background Art

Injuries from insertion of insufflation needles and sharp trocars during laparoscopic surgery continue to occur in spite of a variety of instrument designs and techniques which have been developed to increase safety when accessing the peritoneal cavity.

Attempts to limit injury have used a spring-loaded central shaft or an outer shield that protects the patients tissue from the tip of the insufflation needle and the sharp end of the trocar, respectively. However, these devices provide only limited protection against injury.

The following techniques have also been used:

1. Primary Closed Laparoscopy
   (a) with preliminary pneumoperitoneum
   (b) direct trocar insertion
2. Primary Open Laparoscopy.
3. Secondary Cannula Insertion.

A more detailed discussion of each technique follows:

1) Primary Closed Laparoscopy Technique.

The insertion of the primary cannula is the most dangerous step of the procedure to gain access to the peritoneal cavity. Injuries are produced by the insufflation needle and/or sharp trocar; and the insufflation of gas to create a pneumoperitoneum. This is essentially due to the blind nature of the aforelisted access techniques; and the relative lack of anatomic separation between the abdominal wall and the underlying intraperitoneal and retroperitoneal structures.

The surgeon usually attempts to elevate the abdominal wall with towel clips or manually while inserting the insufflation needle and/or the primary trocar. However, attempting to manually elevate the abdominal wall is often ineffective because of lack of abdominal relaxation. The abdominal wall and intraperitoneal organs are very close together; and the negative pressure within the abdominal cavity makes it difficult to create a space separation between the abdominal wall and the tightly "vacuum-packed" intra abdominal organs. In addition, the maneuvers to elevate the abdominal wall are opposed by the downwards force which must be applied to create a tissue track with the trocar and advance the cannula into position. A larger sharp trocar increases the risk of injury because, with larger trocars an increase in the insertion force may result in unwanted contact with internal organs by the trocar and may hinder the surgeon's control of the trocar.

The complication rate is also influenced by the shape of the distal end of the trocar and anatomical factors. For example, more insertion force is required by a trocar which has a larger outer diameter; or has a conically shaped rather than pyramidal distal end; or is inserted through a thicker or tougher abdominal wall; or is inserted at a 45 degree rather than 90 degree angle, because of the increased resistance of a longer tissue track.

The aforedescribed factors may produce tenting of the peritoneal layer in front of the insufflation needle or primary trocar. This may lead to preperitoneal gas insufflation or to injuries resulting from the attempt to overcome that obstacle.

Creating a preliminary pneumoperitoneum with an insufflation needle may decrease the problem of peritoneal tenting and some of the trocar injuries. Keeping in mind the position of the aorta and other major blood vessels relative to the umbilicus, the patient should be kept off the Trendelenburg position until the insufflation needle has reached the peritoneal cavity. It is known that the surgeon can temporarily increase the pressure of the pneumoperitoneum to 25 mm Hg while inserting a size 10 or larger primary trocar, using a 90 degree angle of insertion and controlling the depth of insertion with a finger or an alternate method as a stopper. The place of choice to insert the insufflation needle and the primary trocar may be the center point of the umbilicus because this is the place where the peritoneum and the fascia are the closest and have their strongest attachments.

However, when using a preliminary pneumoperitoneum the insufflation needle itself often poses a risk of unintended injury to intra abdominal and retroperitoneal structures. In addition, there is a danger of insufflating gas into the wrong body structures, namely, the preperitoneal space, blood vessels, retroperitoneal space, omentum, etc., which may produce additional complications.

The insufflation needle is eliminated with the direct trocar insertion technique. With the direct insertion, visual laparoscopic verification of the correct intraperitoneal position of the cannula is performed before proceeding with the insufflation which may eliminate the aforedescribed complications of insufflation. In this regard the direct visualization of the intraperitoneal organs is more reliable than indirect methods which are employed with an insufflation needle as will be described below.

The direct primary trocar insertion may be safer with smaller and sharper trocars and when used for selected patients who have an abdominal wall which is sufficiently relaxed to be effectively elevated. However, direct trocar injuries actually occur and possibly can be more extensive than those produced by an insufflation needle.

The prior art has not recognized the advantages of substituting an insufflation needle for the sharp trocars and using the insufflation needle with a coaxial outer sleeve and blunt dilator to insert a laparoscopic cannula. As implied in the name "NoTrocar Cannula Insertion System", the prior art sharp trocars are eliminated by using a modified insufflation needle and blunt outer sleeve as a guide to advance a blunt dilator into the needle track and insert the laparoscopic cannula. Contrary to the prior art, the NoTrocar Cannula Insertion System will dilate rather than cut through the tissue track, introducing in sequence the laparoscopic cannula over a specially designed blunt dilator after the blunt dilator has been advanced over the needle guide and reaches the peritoneal cavity. The initial tissue track is formed using a needle instead of using a larger sharp trocar which requires more insertion force and is more difficult to control. The reduced direct local trauma to the wall decreases the risk of injury to epigastric blood vessels, incisional hernia formation and post operatory pain. In addition, the small size of the insufflation needle guide allows insertion into the peritoneal cavity with minimum force, which in turn reduces the risk of unwanted contact with underlying organs.

While a pyramidal sharp trocar requires less insertion force that a conical sharp trocar of equal outer diameter, it produces a wider tissue track in the abdominal wall which is triangularly shaped rather than slit-like. In addition, a pyramidal trocar is more likely to injure the epigastric vessels and require suturing of the fascia to prevent postoperative hernia formation, particularly if the cannula is 10 mm or larger. Compared to the NoTrocar system, the prior art sharp trocars may have a higher risk of laceration to bowel and other intra-abdominal and retroperitoneal structures; and produce more trauma to the abdominal wall which translates in more injuries to blood vessels, post operatory incisional hernia and more post operatory pain.

Compared to the prior art, the safety of the primary closed laparoscopy technique may be improved with the present invention for the following reasons:

a) The O.D. of a 12 gauge insuflation needle is approximately 0.082 inches which is substantially less than the O.D. of the prior art sharp trocars. The sharp trocar of a 5 mm cannula has an O.D. of approximately 0.230 inches and the trocar for a 10 mm cannula has an O.D. of approximately 0.440 inches. After entry into the body cavity, the sharp tip of the insuflation needle is retracted into the outer sleeve guide. The cannula is inserted over a blunt dilator using the insuflation needle guide to advance it into position in the tissue track, thus avoiding large sharp trocars.

b) As discussed above, the decreased insertion force which is required to insert the insuflation needle and the outer sleeve guide facilitates elevating the abdominal wall away from the underlying organs and major blood vessels and avoids tenting of the peritoneum in front of the needle.

c) The reduced trauma to the abdominal wall results in a smaller defect on the fascia may not require closure with sutures and decreases the risk of incisional hernia, injury to epigastric vessels and post operatory pain.

d) Using the NoTrocar insertion system in conjunction with a micro laparoscope allows the surgeon to visually assess the intra-peritoneal positioning of the insuflation needle and outer sleeve guide before performing the insuflation of pneumoperitoneum gas, like it is done with the direct trocar insertion technique. The micro laparoscope fits through the outer sleeve guide and is used after performing the usual testing for placement of the insuflation needle, namely the "drop test", injection and subsequent aspiration of 10 ml of saline solution, comparison of the intra-peritoneal pressures before and after elevating the abdominal wall with the insuflation system closed, etc. The additional safeguard provided by the micro laparoscope may prevent the unintended insuflation of gas into the preperitoneal space, the omentum, the retroperitoneal space, or other structures, including blood vessels, without the potential risk of large sharp trocars used with the direct trocar insertion technique.

Prior art devices such as the VisiPort (made by US Surgical) and the Endopath OptiView (made by Ethicon) are designed for 10 mm or larger cannulas and require a preliminary pneumoperitoneum. Therefore, these devices add little to the safety of primary entry with the insuflation needle and formation of the pneumoperitoneum. These 10/12 mm devices have a hollow, transparent guide rod which fits over the laparoscope and has either a mechanism with retractable blades (VisiPort); or small ridges (OptiView) to create a tissue track under direct visual guidance using a closed insertion technique without utilizing a sharp trocar. Compared to sharp trocar, these devices do not reduce the trauma to the tissue track in the abdominal wall and may represent an increased cost of the procedure. An insuflation needle is required to create a preliminary pneumoperitoneum. The sharp blades and ridges of the VisiPort and OptiView, respectively, still pose a risk to the epigastric vessels and bowel and appear to be as traumatic as the pyramidal trocars. The aforementioned disadvantages may limit the applicability of these devices.

The safety of the closed technique has been improved by the Step cannula made by InnerDyne, which works in a different fashion. The Step cannula uses an expandable sleeve which is introduced into the tissue track over the insuflation needle. The insuflation needle is removed after the pneumoperitoneum is formed. The expandable sleeve is then dilated with a blunt guide rod which is solid (without a channel) and carries either a size 5, 10 or 12 mm cannula. The Step cannula eliminated the sharp trocar, thus reducing the risk of epigastric vessel injuries and damage to the abdominal wall requiring suturing. While the Step cannula represents an improvement, the same results may be reached in a more efficient and cost effective manner. Each Step cannula used must have its own expandable sleeve and sometimes a single port requires more than one expandable sleeve. For example when exchanging cannulas of different sizes a new expandable sleeve may be also required. Suturing and removal of surgical specimens is interfered by the presence of the expandable sleeve which remains around the cannula; and by the excessive length of the Step cannula itself. The bottom line is that the expandable sleeve is unnecessary, cumbersome and costly; and the NoTrocar Cannula Insertion System which does not use them has all of the advantages and none of the disadvantages oft he Step cannula.

2) Primary Open Laparoscopy.

With the prior art technique, the small incision used to enter the abdominal cavity poses its own, albeit reduced, safety problems in terms of properly identifying the peritoneal layer prior to cutting or puncturing through the peritoneum. This crucial step of the Open Laparoscopy is in fact often blind and may explain the bowel and major vessel injuries that have been reported by surgeons using this technique.

The prior art has not recognized the benefits of a new modified primary open laparoscopy insertion technique which is possible with the advent of the micro laparoscope named the Laparoscopic Optically Directed Insertion System ("LODIS").

A micro laparoscope is fitted through the optical sleeve guide which is used to bluntly open the preperitoneum and peritoneal layers through a small skin and fascia incision, using an open technique. Alternatively, the micro laparoscope may be used in conjunction with a sharpened double action 2 mm dissecting clamp to sharply open the peritoneum under direct vision. Both instruments are inserted through a 4.3 mm tubular retractor having a riveted edge to elevate the fascia. After opening the peritoneal cavity, a blunt rod guide is inserted into the peritoneum and the sleeve, the grasper and the scope are removed and the blunt dilator and laparoscopic cannula are then inserted over the rod as described for the Non-Trocar Cannula Insertion System. Stay sutures may not be required to hold the cannula, which is an added advantage. The surgical technique will be discussed in detail below.

3. Secondary Cannula Insertion.

Injury to the epigastric vessels is a frequent complication of the secondary trocar insertion. This injury may occur in spite of careful attempt to visualize the epigastric vessels with the laparoscope or by transillumination prior to inserting the secondary cannulas.

With all the variables being equal in terms of surgical skill, experience of the surgeon and the insertion technique used, a correlation may exist between the size of the outer diameter of sharp trocars and the risk of possible injury to the epigastric vessels or hernia formation which may involve bowel or omentum.

In addition, the secondary trocar possesses a risk of injury of bowel and retroperitoneal blood vessels. A secondary trocar should be inserted under direct laparoscopic guidance, preferably directing the secondary trocar towards the sheath of the primary cannula. It is usually futile to manually attempt elevating the abdominal wall further once an adequate pneumoperitoneum has been formed.

The force that is required to insert the larger sharp trocars and prevent the tenting of the peritoneum may overcome the protection afforded by the pneumoperitoneum. This militates in favor of forming a pneumoperitoneum of adequate size; the use of the smallest size trocar possible; and preferably, the elimination of sharp trocars altogether. The best alternative is the Non-Trocar Cannula Insertion System which is presented next.

One drawback of laparoscopy is the loss of tactile feedback and depth perception. The prior art has not recognized the advantage of allowing the surgeon to touch the tissues directly with his or her fingers. In addition, the prior art has not dealt with the difficulty of restoring the pneumoperitoneum which occurs after the incision in the wall is enlarged. The digital cannula corrects the aforedescribed drawbacks of the prior art.

While addressing the basic desirability of reducing damage to tissue, the prior art has failed to provide a method of entering the body cavity which is easy to use, has a minimum number of parts, allows direct microlaparoscopic verification of peritoneal entry prior to insuflation of the pneumoperitoneal gas, allows for easy and wide dilation of laparoscopic tissue openings, and improves the safety of the access techniques by eliminating the need for a sharp trocar.

SUMMARY OF THE INVENTION

The present invention solves the foregoing problems by providing a coaxial blunt dilator insertion system which uses a coaxial needle guide comprising an insuflation needle and an outer sleeve; and blunt dilator instead of a sharp trocar to insert primary and second laparoscopic cannulas. A single blunt dilator can be used to expand the tissue track to allow insertion of the cannula in a single step. This can be done with any size cannula ranging in size from 2 mm to 23 mm or more. A smaller cannula can be exchanged for a larger cannula by removing the smaller cannula over a guide rod and then inserting a larger cannula over the guide rod with an appropriately sized blunt dilator in a single step.

A guide rod might also be used to insert a 21 mm or larger cannula into the tissue track after a small minilaparotomy or an open laparoscopy has been done (see the digital cannula discussed below). The size of the insertion path can thus accommodate both narrow devices such as 2 mm graspers, scissors, and/or micro laparoscopic optical devices up to and including objects as large as a surgeons finger. A specially designed seal allows insertion of two or more instruments simultaneously through a single 10 or 12 mm cannula to reduce the number of access ports which may be required in excisional procedures such as appendectomies, salpingectomies, oophorectomies, etc. For example, a loop ligature and a grasper can be efficiently operated when inserted together through a single port.

The preliminary pneumoperitoneum for the primary closed laparoscopy technique is performed more safely by first verifying with a micro laparoscope the correct intraperitoneal positioning of the insuflation needle and outer sleeve as it is done with the direct trocar insertion technique.

The open laparoscopy insertion of the primary cannula may be performed under improved visual guidance utilizing the LODIS. A optical needle or blunt optical sleeve guide of appropriate length is fitted over the micro laparoscope and bluntly opens the peritoneum. The optical needle or sleeve guide has been preloaded within an outer sleeve which has been backloaded with a blunt guide rod and a laparoscopic cannula. Alternatively, the micro laparoscope may be used to visually control a sharpened double action grasper to enter the peritoneal cavity.

The digital cannula is sized to allow inserting one finger into the peritoneal cavity. Two different seal ensembles can be interchangeably used with the same cannula to maintain the pneumoperitoneum and to allow the surgeon to alternate use of one finger and 10/12 mm or 5 mm laparoscopic instruments. The finger is used for palpation, dissection and orientation without loss of the pneumoperitoneum or visual control. Specimen removal and suturing is facilitated and operating time may be saved. The digital cannula combines the advantages of a minilaparotomy and laparoscopy and is particularly useful for performing procedures such as ovarian cystectomy, myomectomy, lysis of adhesions, and drainage of pelvic abscesses.

BRIEF DESCRIPTION OF THE DRAWINGS

FIGS. 15A–C illustrate an alternative preferred embodiment of seal ensemble which allows at least two instruments to be inserted simultaneously through the cannula.

DESCRIPTION OF THE PREFERRED EMBODIMENT

Figure 1A:
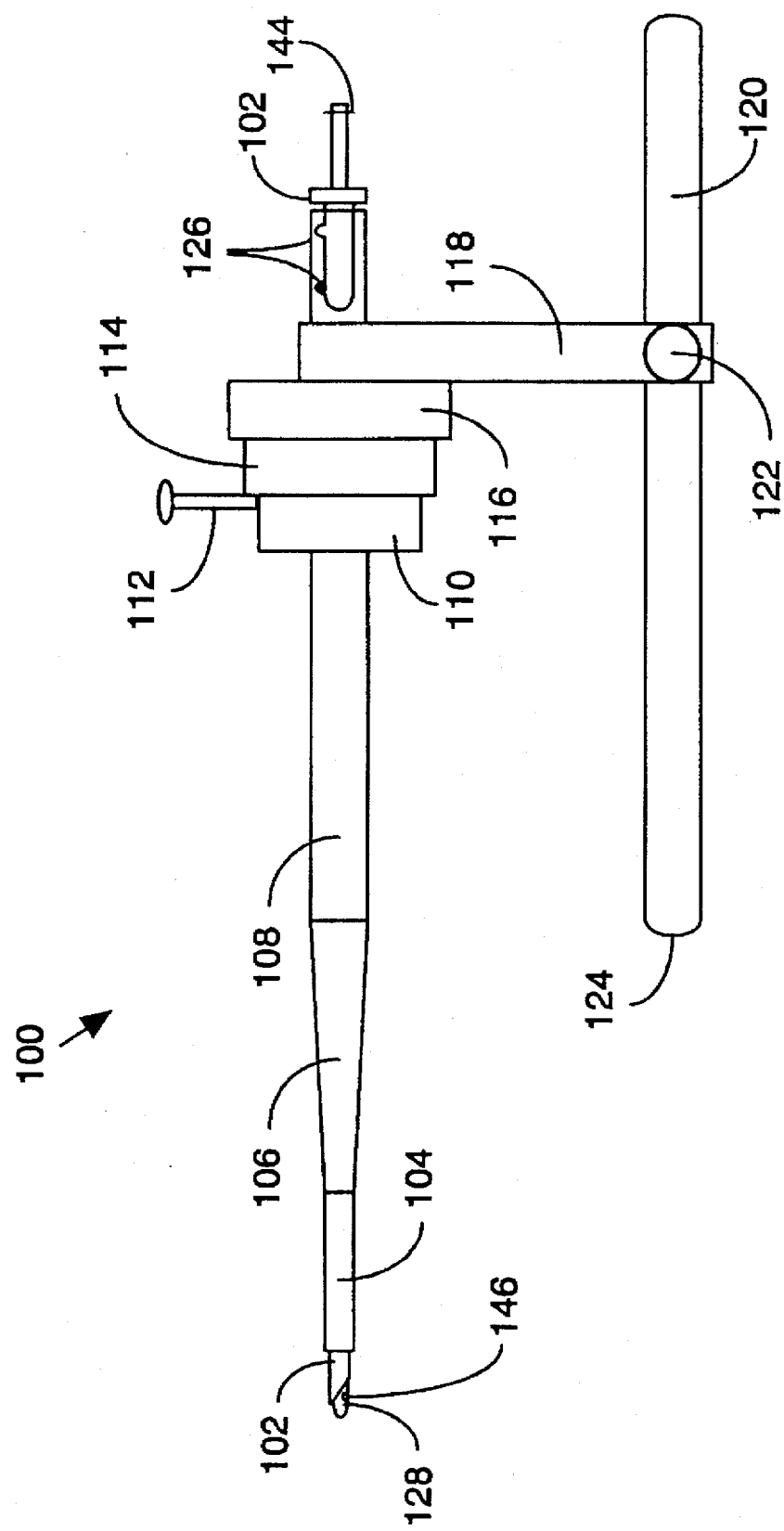
FIG. 1A is a side view of a prior art insuflation needle mounted within a preferred embodiment of the invention with the insuflation needle in the extended position and using a detent mechanism to hold the insuflation needle extended in place within the outer sleeve.

Prior to a discussion of the figures, a general discussion of the features and advantages of the invention will be presented.

The coaxial blunt dilator insertion system (the NoTrocar system) disclosed herein uses a coaxial insufflation needle with an outer sleeve guide and a blunt dilator instead of a sharp trocar to insert first and second laparoscopic cannulas. The closed laparoscopy technique used to insert the primary insufflation needle may be performed in the standard manner. However, before proceeding with the insufflation of gas to create the pneumoperitoneum, a micro laparoscope may be used to directly verify the intraperitoneal position of the sleeve guide which was inserted with the insufflation needle. This feature adds a measure of safety to the closed laparoscopy technique by preventing the gas being insufflated into the preperitoneal space or other anatomical structures, such as omentum, blood vessels, etc.

In addition, the sleeve guide may be converted into a 2 mm cannula by substituting a seal ensemble for the proximal expanded portion, which is detachable. As a result, the sleeve guide not only functions to prevent accidental damage by the tip of the insufflation needle, it also provides a cannula function, as well as acting as a guide sleeve for inserting larger cannulas.

The open laparoscopy insertion of the first cannula may be performed under improved visual guidance utilizing the LODIS. A blunt optical outer sleeve guide of appropriate length is fitted over the micro laparoscope and bluntly opens the peritoneum under visual control. The outer sleeve guide has been backloaded with a blunt obturator and a laparoscopic cannula. Alternatively, the micro laparoscope may be used to visually control a sharpened double action gasper to sharply open the peritoneum. These two instruments are introduced through a 4.3 mm tubular retractor which has a riveted distal end to elevate the fascia with.

A removable handle which is attached to the proximal end of the outer sleeve guide may be gasped with one hand by the surgeon and held over the patient's abdomen to direct and stabilize the position of the sleeve guide within the tissue track and prevent it from advancing too far while pushing the blunt dilator and the cannula into the peritoneal cavity. The blunt dilator forms one body with its proximal handle. The central channel of the dilator snugly but slidably fits over the outer sleeve guide. The cannula is backloaded on the blunt dilator. After the sleeve guide reaches the peritoneal cavity, the dilator and the cannula are simultaneously advanced through the tissue track. A detachable seal ensemble allows suturing, removal of surgical specimens and for the digital cannula, the ability to alternatively use laparoscopic instruments and the surgeon's finger. The pneumoperitoneum may be evacuated and easily formed again, as needed.

In contrast to the prior art sharp trocars, the dilator is blunt and dilates rather than cuts through the tissue track. The coaxial blunt dilator insertion system is safer and less traumatic; it anchors the cannula; it is associated with less post-operatory pain; it reduces the risk of injury to the epigastric vessels, major blood vessels and bowel; and it produces a substantially smaller residual tissue track, thus eliminating the need for suturing to close the fascia after using a size 10 or larger cannula. Costs may likewise be decreased. The passive seal and the detachable seal ensemble of the Lehrer cannulas allows easy suturing, removal of surgical specimens and the exchanging of cannulas. The detachable seal ensemble of the digital cannula allows the surgeon to use either a finger or laparoscopic instruments, alternating use as needed.

The Lehrer digital cannula can be inserted over a rod guide when performing a small minilaparotomy or when substituting a digital cannula for a smaller cannula. The digital cannula can also be inserted over the needle guide in a single step. The digital cannula is sized to allow inserting one finger into the peritoneal cavity. Two different seal ensembles can be interchangeable used with the same cannula, allowing the surgeon to alternate use of one finger and 10/12 mm laparoscopic instruments and maintain the ability to form again the pneumoperitoneum. The finger is used for palpation, dissection and orientation without loss of the pneumoperitoneum or visual control. Specimen removal and suturing is facilitated and operating time may be saved. The digital cannula combines the advantages of a minilaparotomy and laparoscopy and is particularly useful for performing procedures such as ovarian cystectomy, myomectomy, lysis of adhesions, drainage of pelvic abscesses, etc.

The NoTrocar cannula insertion system for primary and secondary laparoscopic cannulas disclosed herein uses a needle guide which comprises a needle with a sharp, beveled distal end; which has a spring loaded safety shaft that occupies the central channel of the needle and in the resting position extends past the end of the needle and is standard with insuflation needles; and a blunt outer sleeve which slidably fits over the needle. The proximal end of the needle may be fixedly attached to an expanded segment which is approximately 5 cm in length; houses the spring of the safety shaft of the needle; has a retainer pin; and is shaped like a Luer lock connector at the proximal end. Alternatively the expanded segment of the needle may be screwed over a threaded collar which is fixedly attached to the proximal end of the needle. Further, a collet may be used to attach a removable outer sleeve and/or adjust its length relative to the distal end of the needle.

Several lengths of insuflation needles may be manufactured. In the preferred embodiment, a single length of needle guide fits cannulas 5 through 12 mm. The insuflation needle has a spring-loaded central safety shaft (which is standard with prior art insuflation needles) and extends about 1 mm past the tip of the insuflation needle; retracts into the central channel of the needle during the insertion through the tissues; and allows the flow of insuflation gas through one or more side openings. The proximal ends of the insuflation needle and outer sleeve have expanded sections which use a notched retainer in conjunction with a spring retractor to hold the needle in either the extended or retracted position relative to the distal end of the outer sleeve. In the alternative, the proximal ends of the insuflation needle and outer sleeve can use a non-spring manual detent to hold the needle in either the extended or retracted position relative to the distal end of the outer sleeve. In the rest position, the coil spring keeps the sharp distal end of the needle retracted within the outer sleeve. The spring can be used to facilitate advancing the outer sleeve over the needle tip upon entry into the peritoneal cavity. The two notches placed at each end of the slot in the expanded portion of the outer sleeve form detents to hold the needle in either the extended or retracted position relative to the distal end of the outer sleeve.

The total length of the aforedescribed needle is approximately 26 cm to 30 cm, or 10–12 in. Of course, those skilled in the art will understand that the length of the needle may vary depending on the length of the cannula it will be used with; and its intended use for slim or obese patients. The portion of needle extending past the distal end of the blunt dilator is controlling and must exceed the thickness of the abdominal wall. A needle guide of a single length and gauge can be used for cannulas size 5 mm, 7 mm, 10 mm, and 12 mm.

The tolerance between the needle and its outer sleeve may be airtight, preventing the pneumoperitoneal gas from leaking through while allowing the insulation needle to slide in and out through the outer sleeve. However, a larger tolerance may require placing a detachable seal ensemble on the outer sleeve of the needle guide which is similar to the other cannulas, and allows using the outer sleeve as a 2 mm cannula for micro laparoscopic instruments.

The handle slidably fits on a collar at the distal end of the expanded portion of the outer sleeve. To load the components of the system, the handle must be backloaded first, before the blunt dilator and the cannula are backloaded. The surgeon can stabilize the handle with one hand against the surface of the abdomen while inserting the blunt dilator and cannula to prevent the excessive penetration of the outer sleeve into the abdominal cavity. This maneuver is facilitated by means of the aforedescribed adjustable handle, but may be performed without the handle.

The outer sleeve has a blunt distal end. On the proximal end, it is attached to an expanded segment which is tubular, has a longitudinal slot with two notches, and slidably accepts the expanded segment of the needle which holds the retainer pin. A coil spring allows the sharp needle to be rapidly retracted into its outer sleeve upon entry to the peritoneal cavity. The retracted position is also referred to as the resting position. In the preferred technique, upon entry to the peritoneal cavity the position of the insuflation needle relative to the needle track is stabilized and the coil spring is released by disengaging the spring retainer to facilitate advancing the outer sleeve past the distal end of the insuflation needle. When the retainer pin is positioned into the distal notch, the beveled tip of the needle is extended past the distal end of the outer sleeve; the coiled spring is compressed; and the distal end of the expanded segment of the needle is close to the bottom of the expanded tubular segment of the outer sleeve.

Commercially available micro laparoscopes such as the Imagyn micro laparoscope which measures 1.98 mm O.D. which is 0.79" O.D. and fits within the I.D. of the outer sleeve guide. Verification of the intraperitoneal position of the sleeve may be obtained in real time. At this point, the distal end of the outer sleeve should be immediately advanced about one or two centimeters into the peritoneal cavity and stabilized with the adjustable handle. The micro laparoscope is then withdrawn to start the insuflation through the insuflation needle or through the seal ensemble. The blunt dilator and cannula are then inserted as shown in the figures discussed below.

The outer sleeve fits snugly but slidably into the central channel of the blunt dilator. The distal segment of the central channel of the dilator is only 1 or 2 mm long and is narrower than the rest of the obturator's central channel. Its tolerance around the needle's outer sleeve is about 0.002" which provides a smooth transition and prevents entrapment of tissue or leakage of gas. No seal is required to avoid leakages of pneumoperitoneal gas through the central channel of the dilator. However, if necessary, a seal may be easily attached at the proximal end of the expanded handle of the dilator.

The dilator comprises a distal segment, a shaft and an expanded handle. These components form one single body. The distal segment of the dilator has a tapered portion with a 70 degree slant, approximately; and a non-tapered portion. In the prototype of the 5 mm cannula the length of these two portions is about 10 mm and 7 mm, respectively; and in the prototype of the 10 mm cannula, the corresponding lengths are about 33 mm and 14 mm, respectively. The distal segment of the dilator fits snugly within the cannula, whose tapered distal end provides for a smooth transition. Once the outer sleeve reaches past the peritoneal layer, both the dilator and the cannula may be simultaneously advanced through the tissue track by pushing on the handle of the dilator. The outer diameter of the dilator is smaller on the shaft than on its distal segment, to facilitate sliding it through the seal of the cannula.

The preferred embodiments of the coaxial blunt dilator insertion system cannulas are 5, 7, 10 and 12 mm in size and their length varies from 55 to 130 mm. The outer sleeve guide can be turned in a 2 mm microlaparoscopic cannula by interchanging its proximal portion for a detachable seal ensemble.

The digital cannula has an I.D. suitably sized to accept the finger of a surgeon. Of course, those skilled in the art will recognize that individual surgeons will use different sized digital cannula to accommodate their fingers. The shaft fits slidably but snugly over the blunt dilator. A gloved index finger with an additional latex sheath easily fits within the central channel of the cannula after the blunt dilator has been removed. The latex sheath is attached to the shaft of the cannula with a O-ring which has been preloaded on the surgeon's finger and fits over the proximal threaded collar of the shaft. Without the seal ensemble, the shaft measures about 5 to 6 cm in length such that the distal segment of the index finger past the distal finger joint may be extended past the distal end of the shaft. After the cannula has been inserted into the tissue track and the peritoneal cavity, the seal ensemble may be easily attached to the shaft of the cannula to continue the procedure using 5 or 10 mm laparoscopic instruments instead of the surgeon's finger. To insert the primary cannula using the closed laparoscopy technique, the NoTrocar system uses the following steps:

1) Insertion of the insuflation needle and outer sleeve through the abdominal wall.
2) Insertion of the micro laparoscope through the outer sleeve to verify intraperitoneal positioning of the outer sleeve.
3) Creation of the pneumoperitoneum.
4) Insertion of the cannula over the blunt dilator and the needle guide.

The technique used to insert the insuflation needle is the same standard technique used with the prior art Veress needle.

The outer sleeve is inserted at the same time as the insuflation needle and accepts a micro laparoscope. This feature allows the surgeon to verify the intraperitoneal position of the needle guide before proceeding with creation of the pneumoperitoneum, as is done with the direct trocar insertion technique. The advantage of using the micro laparoscope through the outer sleeve is that the larger sharp trocars are not required, contrary to the primary direct trocar insertion technique. The invention avoids the large mount of damage created by the trocar because of the smaller size of the outer sleeve, because the force required to penetrate the abdominal wall is less, and because the surgeon is able to better control the insuflation needle rather than the sharp trocar.

The sharp end of the insuflation needle is kept securely retracted within the outer sleeve while creating the pneumoperitoneum and bluntly inserting the cannula and dilator into the tissue track over the Lehrer insuflation needle guide. In comparison to the prior art sharp trocars, the tissue track will better anchor the cannula without the need of threads because its elasticity is preserved by the blunt dilatation. This further decreases trauma to the tissues.

Insertion of larger cannulas may be facilitated by infiltrating the fascia and muscle along the needle track with 10 ml of saline or with a long acting local anesthetic; and/or applying a suitable lubricant on the dilator. The skin must be incised with a scalpel, as in the prior art.

When performing the open laparoscopy technique to insert the primary cannula, the blind puncture through the peritoneum can be avoided with the aforedescribed techniques which are performed either under direct view or under the direct guidance of the micro laparoscope.

For open laparoscopy, LODIS may be preferable to the currently practices blind puncture through the peritoneum. The optical Lehrer sleeve guide may be used alone to bluntly dissect and open the peritoneum. Alternatively a micro laparoscope may be used in conjunction with a 2 mm double action grasper or dissector. These two instruments are introduced through a 4.3 mm tubular retractor which has a riveted distal end to elevate the fascia with, allowing a smaller incision on the skin and fascia.

Alternatively, the Lehrer needle guide can be used in open laparoscopy without the micro laparoscope, as follows: The wall suction may be attached to the insuflation needle using the provided gas insufflation port. When the insufflation needle is placed in the retracted position within the outer sleeve, gas is input to the abdominal cavity to elevate the peritoneal wall. Used in combination with a double action 2 mm grasper, the preperitoneal and peritoneal tissues may be opened bluntly with the Needle guide; or by a spreading apart action with the grasper.

A single Lehrer insufflation needle guide may be used to insert the primary cannula and all the secondary cannulas. A single cannula obturator may be used for all the cannulas of same size.

To insert secondary cannulas, the insufflation needle may be attached to a syringe to infiltrate the needle track with saline or with a dilute solution containing a long acting local anesthetic. Using the syringe, asphation may be performed while advancing the needle under laparoscopic guidance, to ensure the integrity of the epigastric vessels. If a bloody tap is encountered, applying external pressure for a few minutes against the counter pressure of the pneumoperitoneum will likely stop further bleeding without the need for suturing or electro surgery. Once in the peritoneal cavity, the needle tip is retracted into the outer sleeve prior to proceeding with the insertion of the obturator and cannula. The Lehrer needle guide is best directed towards the primary sleeve to visually control the cannula insertion.

Referring to FIG. 1A, this figure shows a prior art insuflation needle mounted within a preferred embodiment of the cannula insertion system 100 with the insuflation needle 102 in the extended position. An inner spring loaded blunt tube 128 is typically used in the prior art insuflation needle 102. A pinhole 146 is near the distal end of blunt tube 128 to allow gas that is insufflated through the Luer lock connector 144 at the proximal end of the needle to pass into the peritoneal cavity. The insuflation needle 102 is slidably mounted within the outer sleeve guide 104. Outer sleeve guide 104 is slidably mounted within first dilator 106. First cannula 108 is backloaded onto first dilator 106 prior to insertion into a patient. First cannula 108 has a threaded seal base 110 and a gas insuflation port 112 with a Luer lock connector. First seal cap 114 encloses an elastic seal 302 (shown in FIGS. 3 and 15B). Dilator handle 116 is attached to the proximal end of dilator 106, and in the preferred embodiment is formed from one body. In the preferred embodiment, dilator handle 116 fits over the edge of seal cap 114 to provide a more secure grip for the surgeon's hand.

Handle offset 118 offsets handle 120 to the side of sleeve guide 104 and is adjustable via knob 122 to vary the distance between distal handle end 124 and the distal tip of sleeve guide 104. By adjusting knob 122, the surgeon can vary the depth of penetration of the device into the body cavity by holding the handle at the distal end and against the surface of the abdominal wall. An advantage of this procedure is that accidental injuries due to over penetration can be avoided.

Also illustrated in this figure are detents 126 which lock insuflation needle 102 in the extended or retracted positions. The distally located detent 126 is used to secure the insuflation needle 102 in the extended position and the proximally located detent 126 is used to secure the sharp end of the insuflation needle 102 in the retracted position within the outer sleeve 104.

Figure 1B:
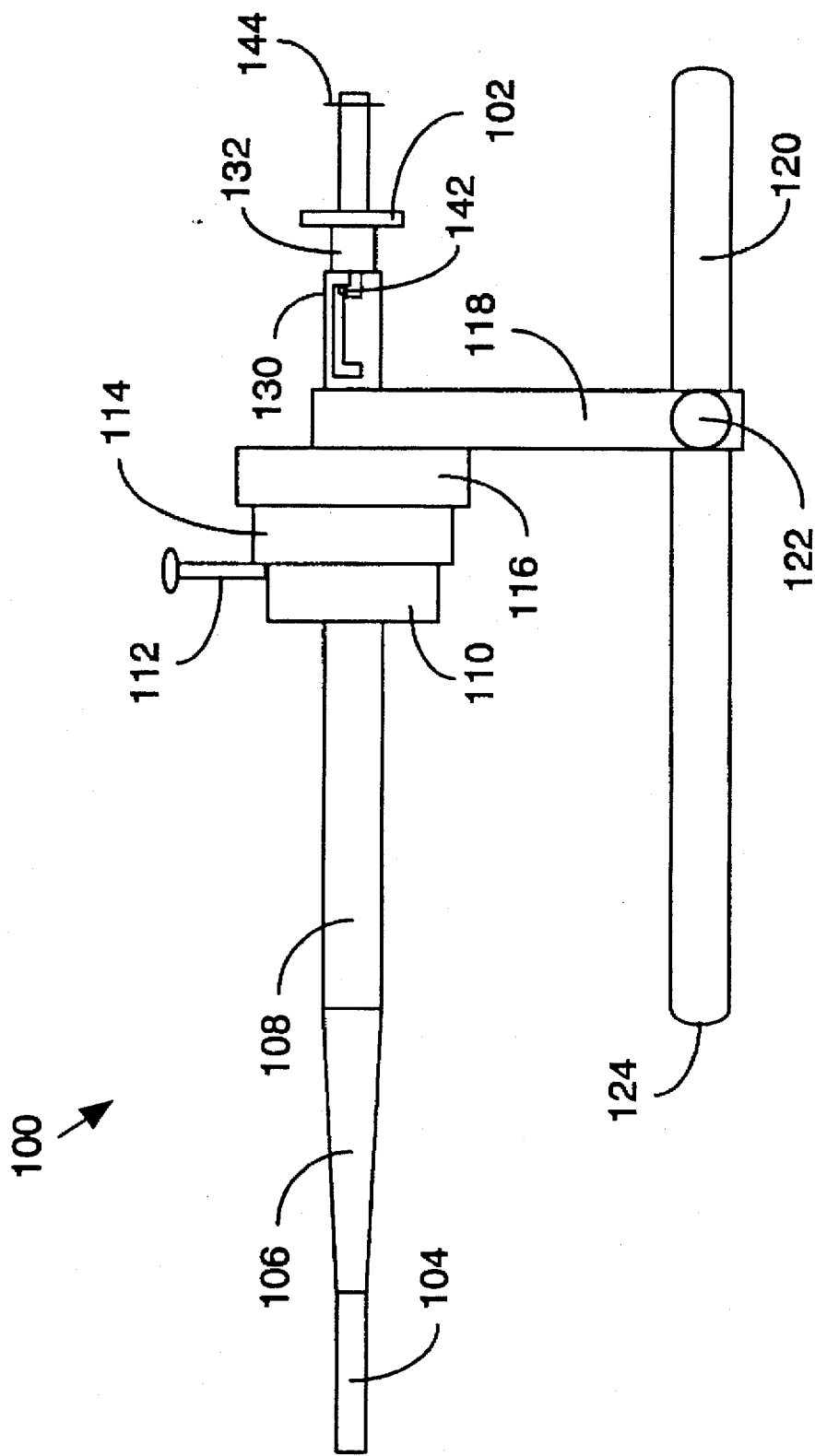
FIG. 1B is a side view of an alternative preferred embodiment of the cannula insertion system having a spring loaded retractor mechanism instead of the detent mechanism shown in FIG. 1A.

FIG. 1B illustrates an alternative to the detent mechanism shown in FIG. 1A. This embodiment uses a spring loaded retractor 130 which automatically withdraws insuflation needle 102 to the rest (or retracted) position. The spring loaded retractor 130 uses a spring 140 (shown in FIG. 1C) which is enclosed in a spring guide 132. Those skilled in the art will recognize that the outer sleeve guide 104 can be a detachable sleeve that is held in place by a conventional collet structure. By allowing the outer sleeve guide 104 to be detachable and adjustable in length, it can be used in conjunction with a longer needle to support longer and wider dilators 104. A Luer lock connector 144 is shown on the proximal end of the needle.

Figure 1C:
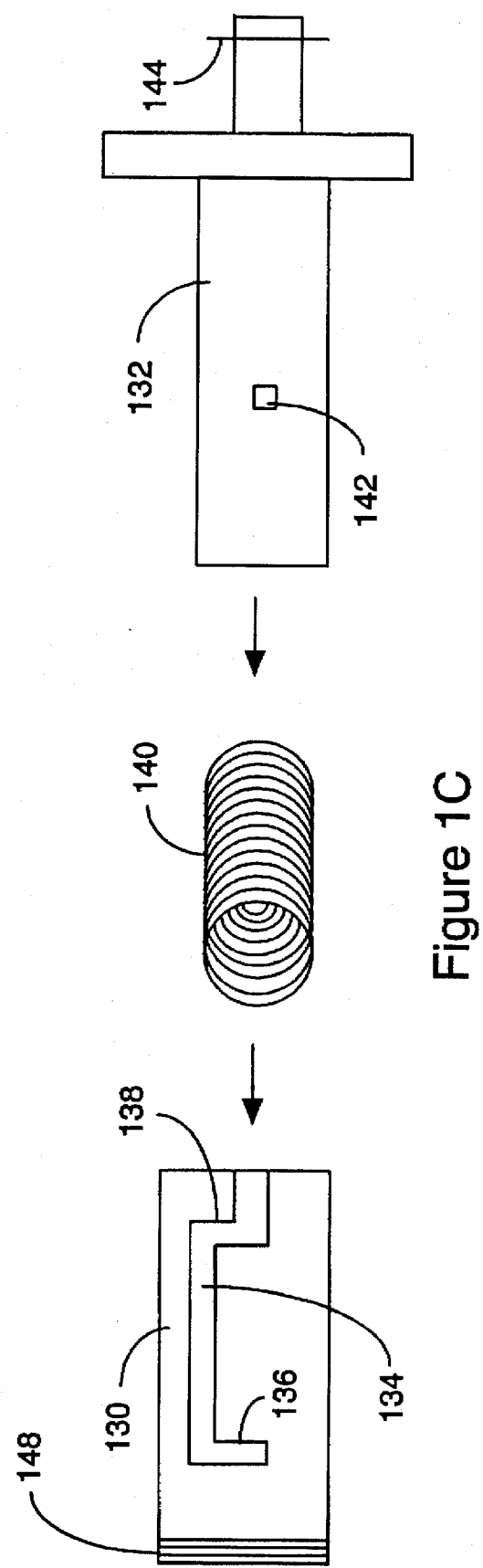
FIG. 1C is an exploded view of the spring loaded retractor mechanism shown in FIG. 1B.

FIG. 1C is a closeup view of the spring loaded retractor 130, the spring guide 132, and spring 140. Spring 140 fits within spring guide 132 which in turn fits within spring retractor 130. A retaining pin 142 slides within slot 134. In the extended position, retaining pin 142 rests against wall 136 and in the retracted position retaining pin 142 rests against wall 138. Optional threads 148 allow the spring retainer 130 to be removed and replaced with a seal ensemble 110, 114 (shown in FIG. 1E). As a result, the outer sleeve guide 104 can be used as a 2 mm cannula.

Figure 1D:
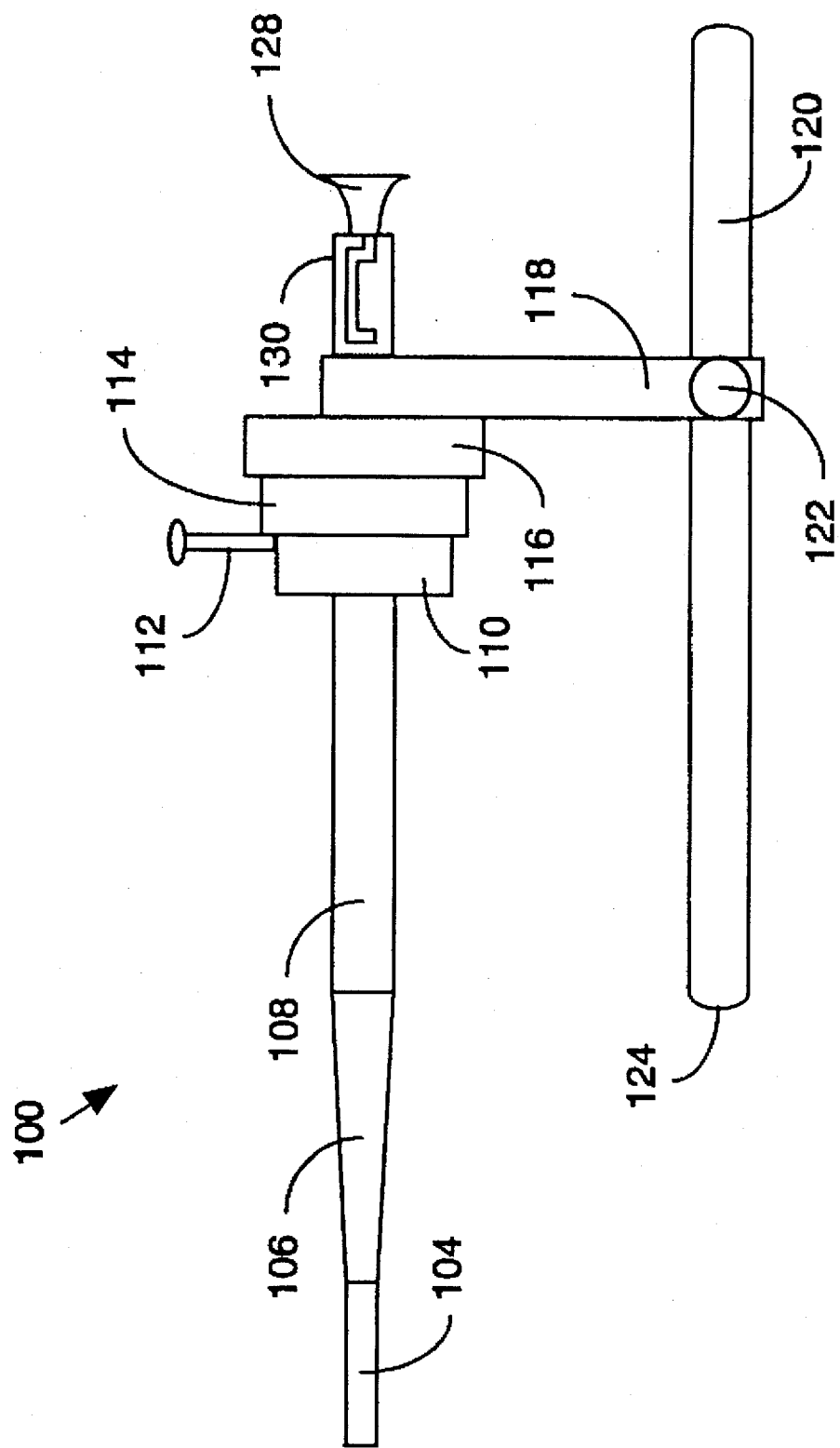
FIG. 1D is a side view of FIG. 1B with the insuflation needle removed and a micro laparoscope inserted in its place.

FIG. 1D illustrates the cannula insertion system of FIG. 1B with the insuflation needle 102 withdrawn and replaced with an optical device 128 (typically a micro laparoscope). This embodiment allows the surgeon to see exactly where the device is positioned while using it as a blunt dissector in open laparoscopy. Those skilled in the art will also recognize that optical device 128 can have a sharpened distal end so that it can be used to penetrate the body cavity wall in place of the insuflation needle 102.

Those skilled in the art will further recognize that insuflation needle 102 can be a hollow needle or have a spring loaded shaft which is standard with insuflation needles. Likewise, insuflation needle 102 can be replaced with an optical device with a blunt end. The use of an optical device will allow the surgeon to observe what the needle is touching during blunt dissection in open laparoscopy, thereby providing an extra margin of safety to the patient during surgery and permitting a reduction in the size of skin and fascia incision.

Figure 1E:
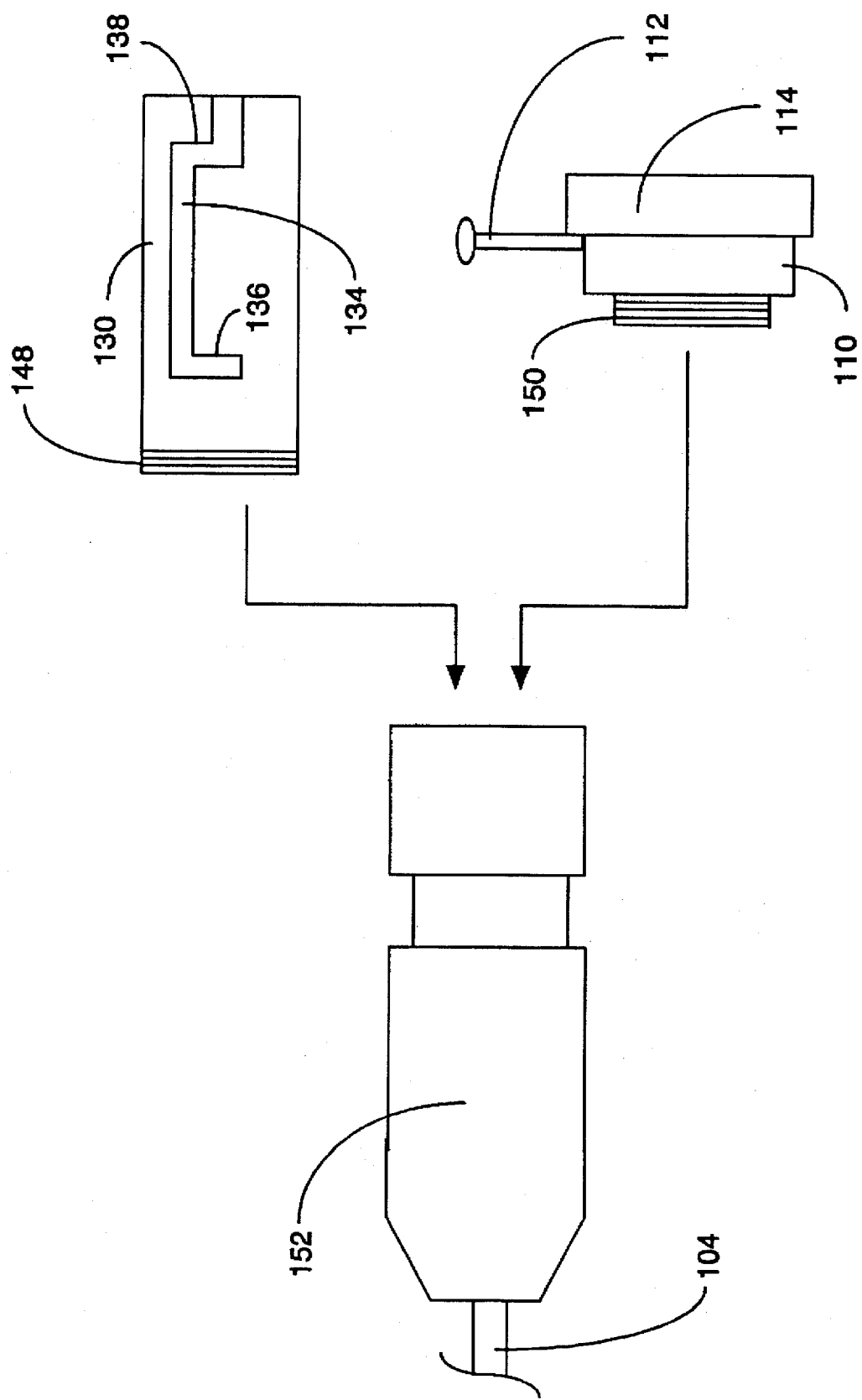
FIG. 1E illustrates a detachable embodiment of the spring loaded retractor mechanism shown in FIG. 1C. The spring retractor mechanism in this embodiment can be interchangeably replaced with a seal ensemble to convert the outer sleeve into a 2 mm cannula. A collet allows the outer sleeve to be adjusted or even be replaced.

In FIG. 1E, a threaded removable embodiment of spring retractor 130 is shown. Threads 148 are unscrewed from collet assembly 152. Thereafter, a seal ensemble 110, 112, 114 can be inserted into collet 152 to convert outer sleeve 104 into a 2 mm cannula.

Figure 2:
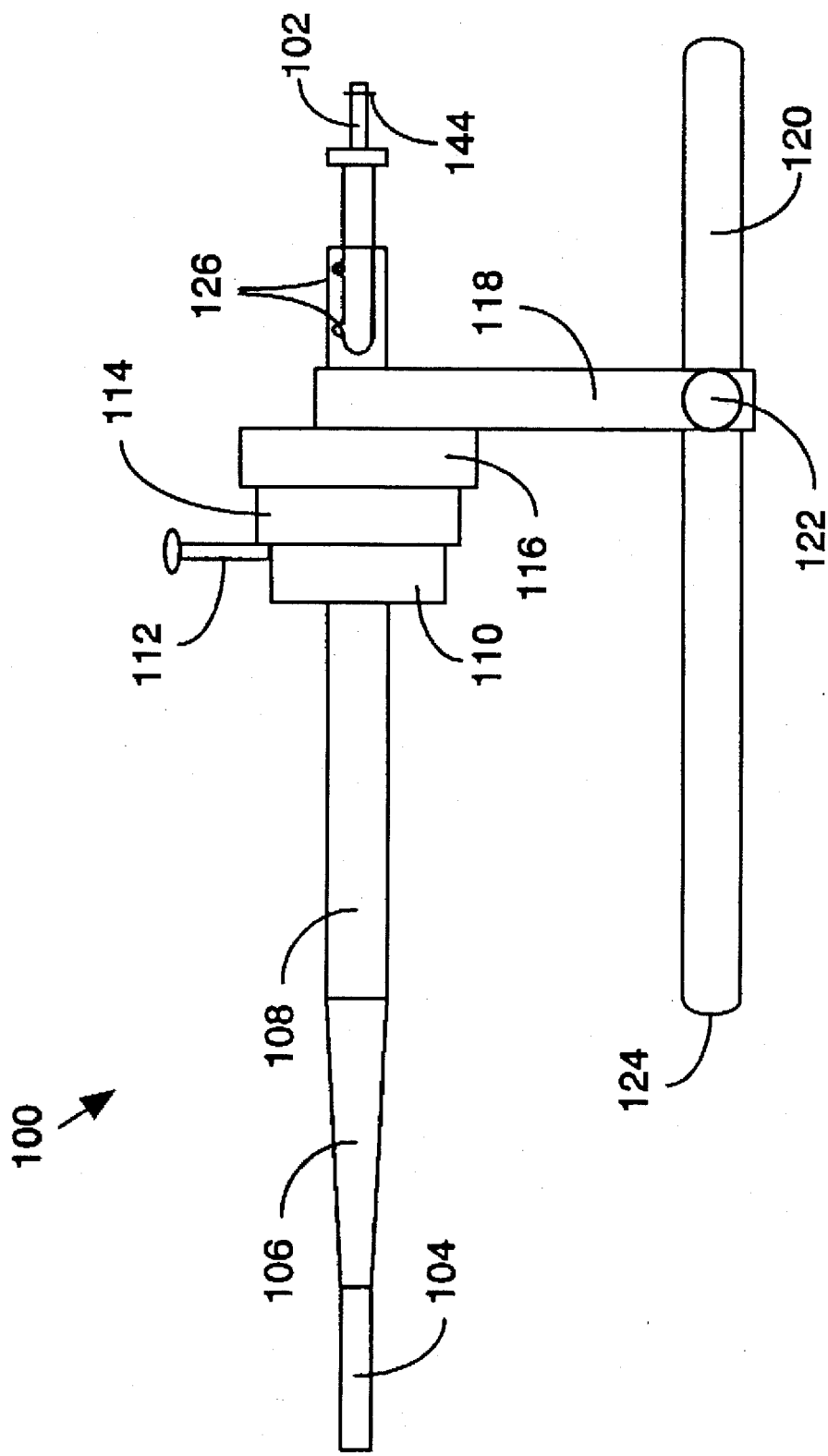
FIG. 2 is a side view of an insuflation needle mounted within the embodiment of FIG. 1A with the insuflation needle in the retracted position.

In FIG. 2, insuflation needle 102 is shown in the retracted position. As can be seen, the distal tip of insuflation needle 102 is withdrawn into outer sleeve guide 104. As a result, the tissue of a patient is protected from accidental damage when the device is inside the peritoneal cavity. The first line of protection is the retractable spring loaded shaft within the needle which is less safe than retracting the needle within the outer sleeve.

Figure 3A:
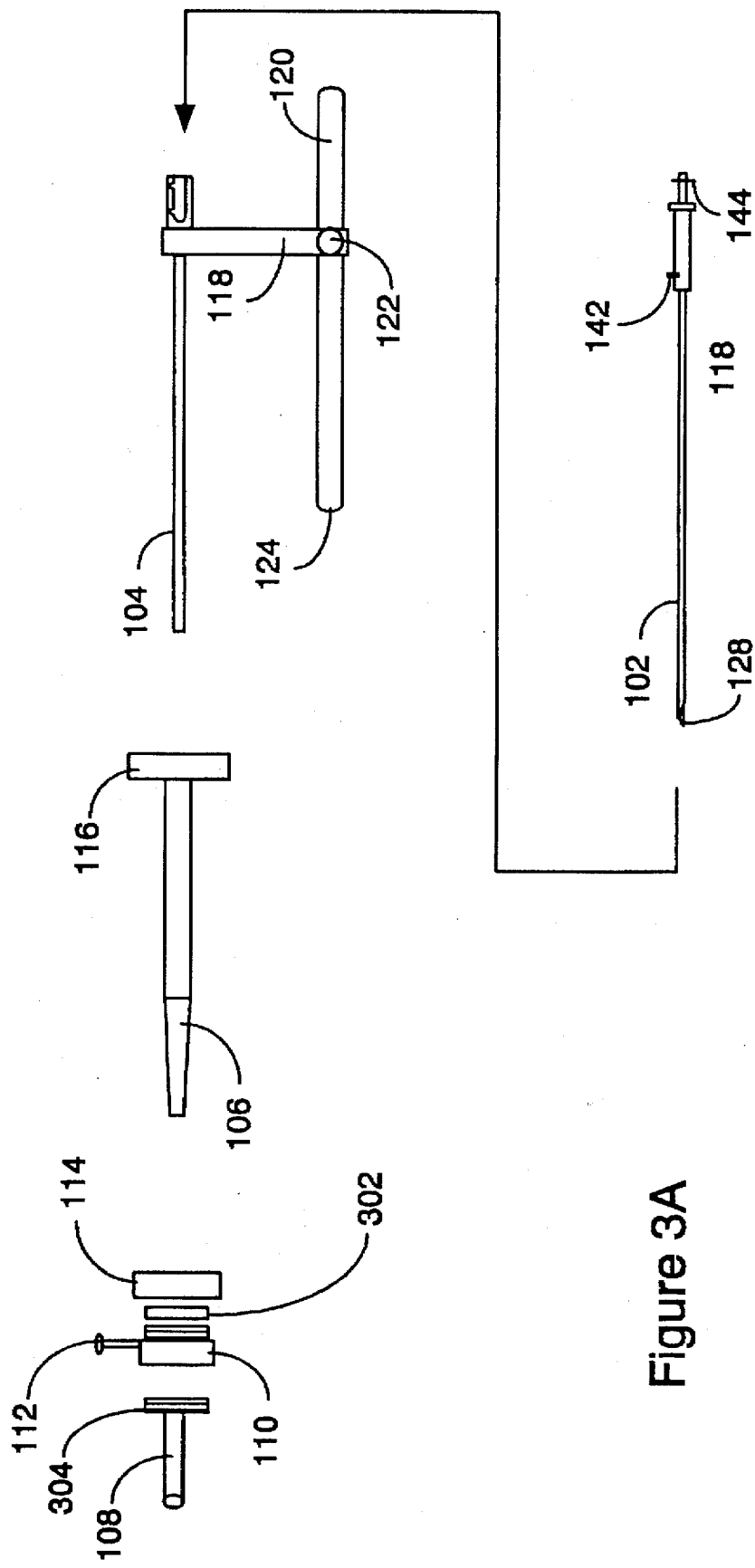
FIG. 3A is an exploded view of the cannula insertion system shown in FIG. 1A.

FIG. 3A shows an exploded view of the cannula insertion system 100. Also shown in this figure is elastic seal 302 which prevents gas leakage when first cannula 108 is inserted in the peritoneal cavity. Cannula 108 has a threaded cannula base 304 to permit attachment to seal ensemble 110, 112, 114. This figure illustrates the detent version of the device shown in FIG. 1A.

Figure 3B:
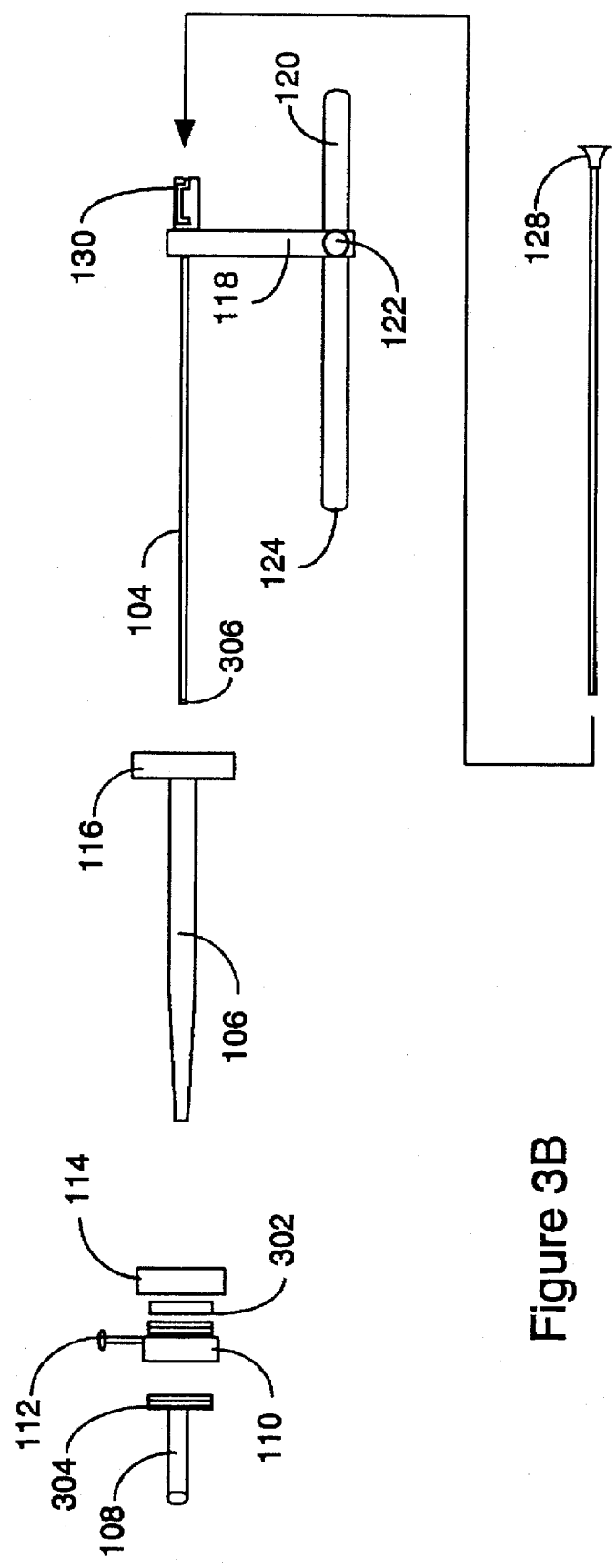
FIG. 3B is an exploded view of the cannula insertion system shown in FIG. 1D.

FIG. 3B shows an exploded view of the cannula insertion system 100 with an optical device 128. This figure differs from FIG. 3A in that it illustrates the optical sleeve guide used for blunt dissection during open laparoscopy which has been backloaded with the blunt dilator and the cannula. Also, an optical insert 306, which is made of neutral fiber optical material, is shown fixedly attached to the distal end of outer sleeve guide 104.

Figure 4:
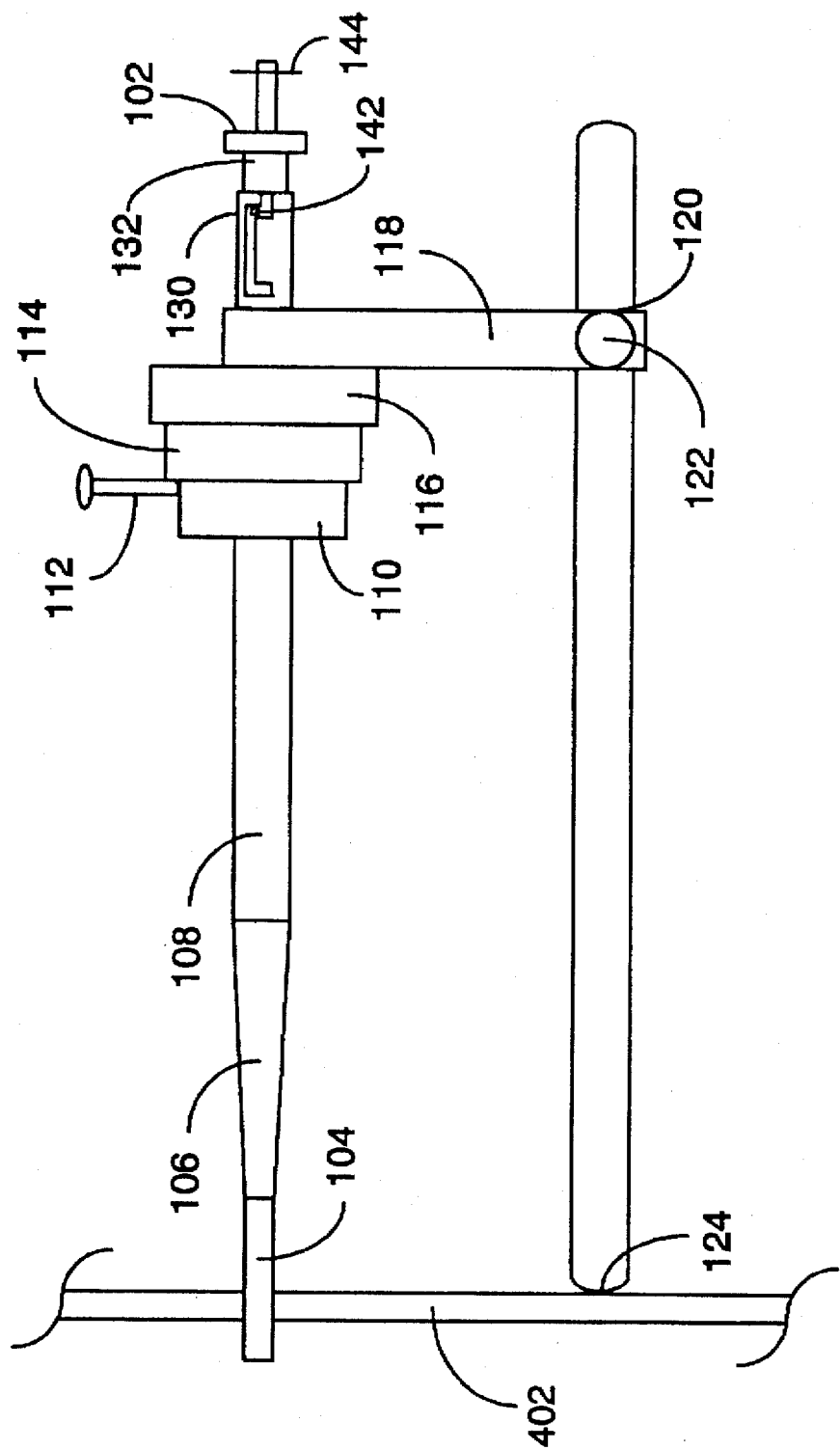
FIG. 4 shows the cannula insertion system with its outer sleeve guide inserted through the abdominal wall, the insuflation needle in the retracted position and the handle adjusted to control penetration depth of the outer sleeve guide.

FIG. 4 shows the outer sleeve guide 104 inserted through the peritoneal wall layer 402 of the patient. After the device has penetrated the peritoneal wall 402, the surgeon retracts needle 102 and then adjusts handle 120 to place the distal end of handle 120 near the abdominal wall to prevent excessive penetration of the outer sleeve guide 104 into the peritoneal cavity. This is important because each patient will vary in size and the ability to adjust penetration depth will enable the surgeon to avoid unnecessary injury to the patient.

Figure 5:
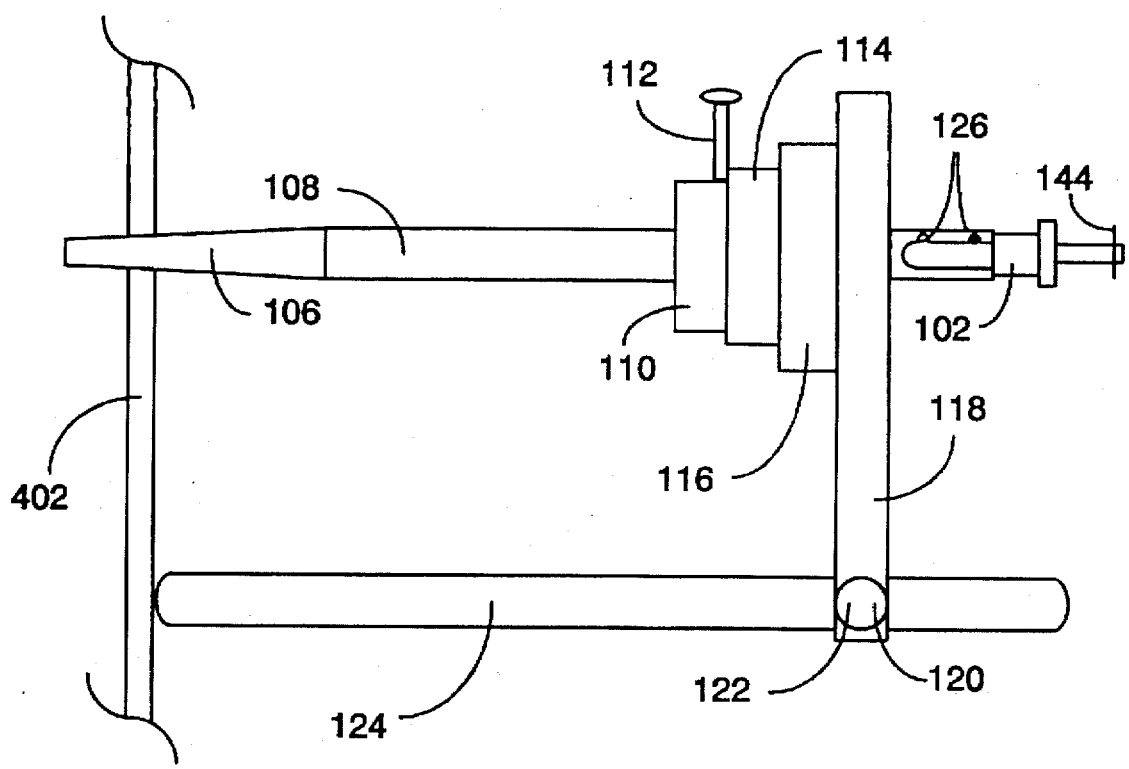
FIG. 5 shows the cannula insertion system with the insuflation needle retracted within its outer sleeve; with the handle adjusted to prevent excessive penetration of the distal end of the outer sleeve; and with its blunt dilator inserted through the abdominal wall and past the distal end of the outer sleeve.

FIG. 5 illustrates the cannula insertion system 100 after insertion of the blunt dilator 106 into the peritoneal cavity and after the insuflation needle 102 and outer sleeve guide 104 have been removed. The blunt dilator 106 is shown inserted through the peritoneal layer 402 of the abdominal wall and past the distal end of the outer sleeve guide 104 which is being held in position with the handle 120.

Figure 6:
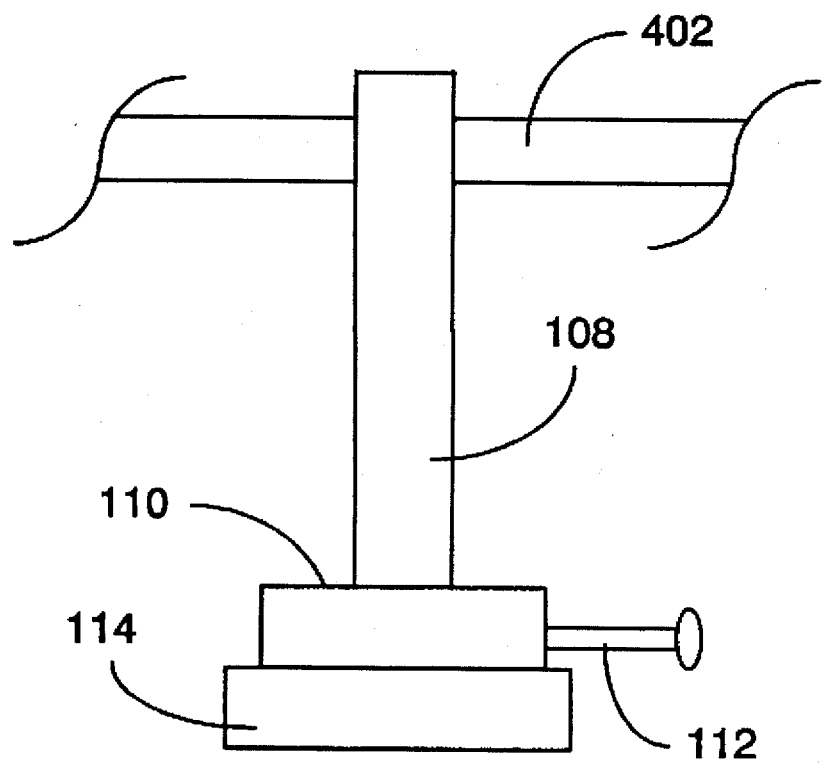
FIG. 6 shows the first cannula of the NoTrocar cannula insertion system inserted through the abdominal wall after the remainder of the NoTrocar cannula insertion system has been removed.

FIG. 6 illustrates the first cannula 108 inserted into the peritoneal cavity, after which the dilator 106, insuflation needle 102, outer sleeve guide 104, and handle 120 have been removed.

Figure 7:
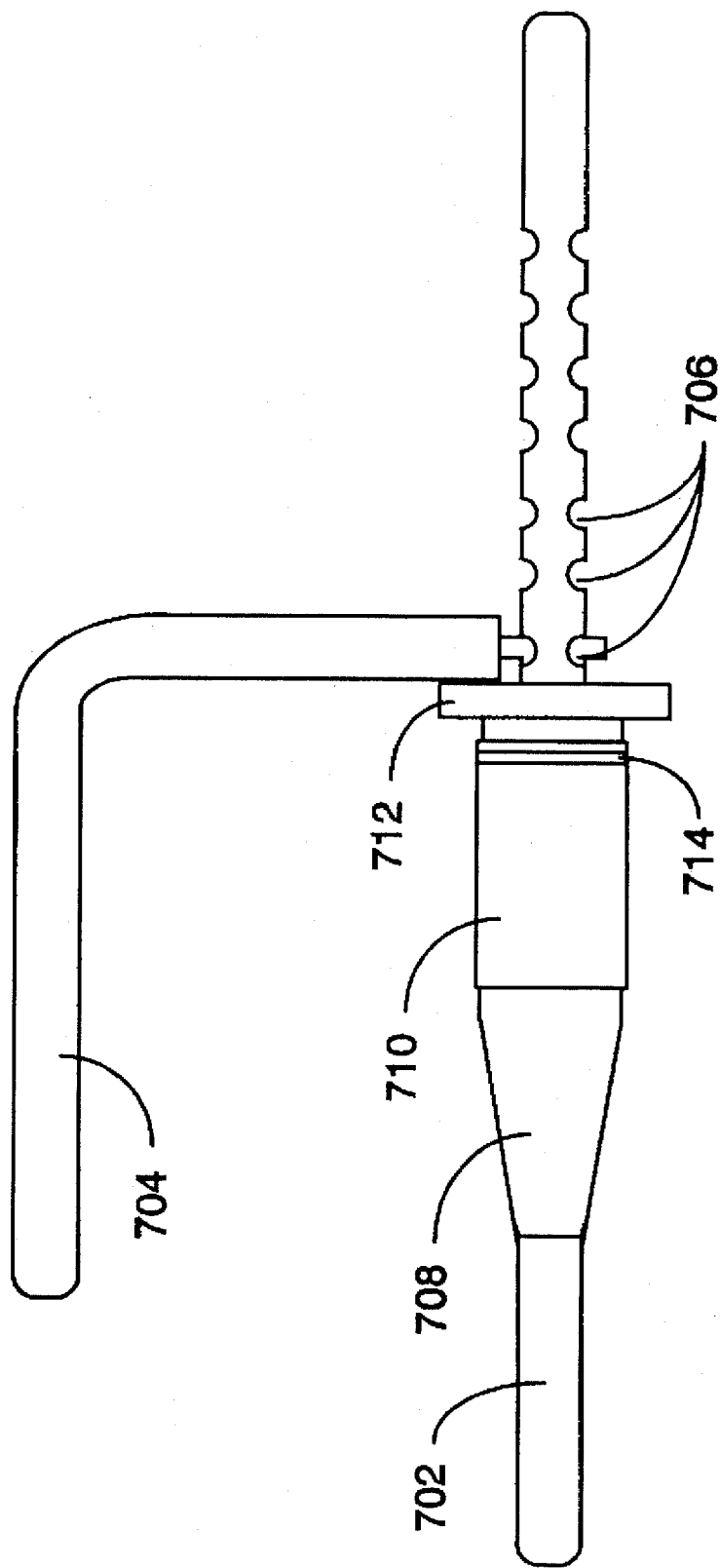
FIG. 7 is a side view of a preferred embodiment of the second cannula of the NoTrocar digital cannula insertion system. A seal ensemble may be attached after removing the blunt dilator and guide rod.

FIG. 7 is a side view of a prefected embodiment of the second cannula 710 (described interchangeably as the digital cannula 710) used with the cannula insertion system 100. A second guide rod 702 has apertures 706 to attach a second handle 704. Second handle 704 serves the same purpose as handle 120 in the cannula insertion system 100. It is adjusted by moving from one aperture 706 to another as required to place the distal end of handle 120 on the surface of the abdominal wall. Second dilator 708 and digital cannula 710 are shown mounted on second guide rod 702. Dilator handle 712 is used to push digital cannula 710 and dilator 708 simultaneously into the tissue track over the guide rod 702. Dilator handle 712 is integrated into a single unit with dilator 708 in the preferred embodiment.

Second handle 704 illustrates an alternative embodiment of handle. In this embodiment, penetration depth is varied by moving handle 702 to different aperture locations on guide rod 702 rather than by adjusting knob 122 as was done with first handle 120. While two separate handle configurations were used for discussion purposes, those skilled in the art will recognize that once the concept of an adjustable offset handle used to control body cavity penetration is understood, the offset handle can be implemented such that a single handle is used in place of first handle 120 and second handle 704. As a result, the device can be further simplified and costs can be further reduced.

Figure 8:
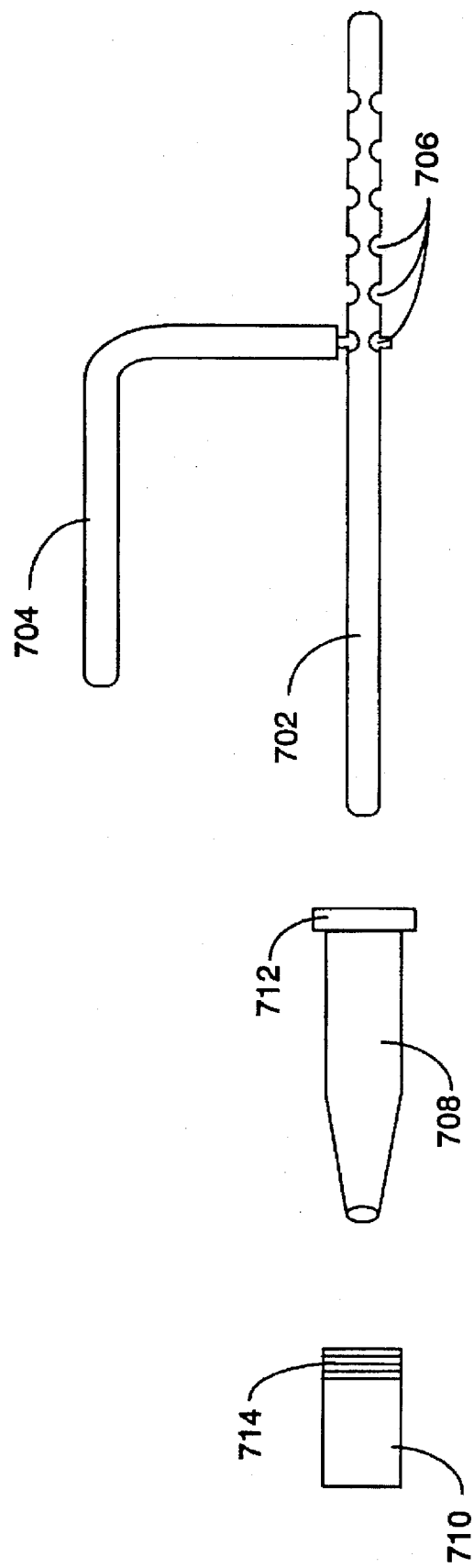
FIG. 8 is an exploded view of a preferred embodiment of the second cannula of the cannula insertion system. The above described seal ensemble is not shown.

FIG. 8 shows an exploded view of the cannula insertion system 100. This view illustrates second (digital) cannula 710 in relation to dilator handle 712, second dilator 708 and second handle 704.

Figure 9:
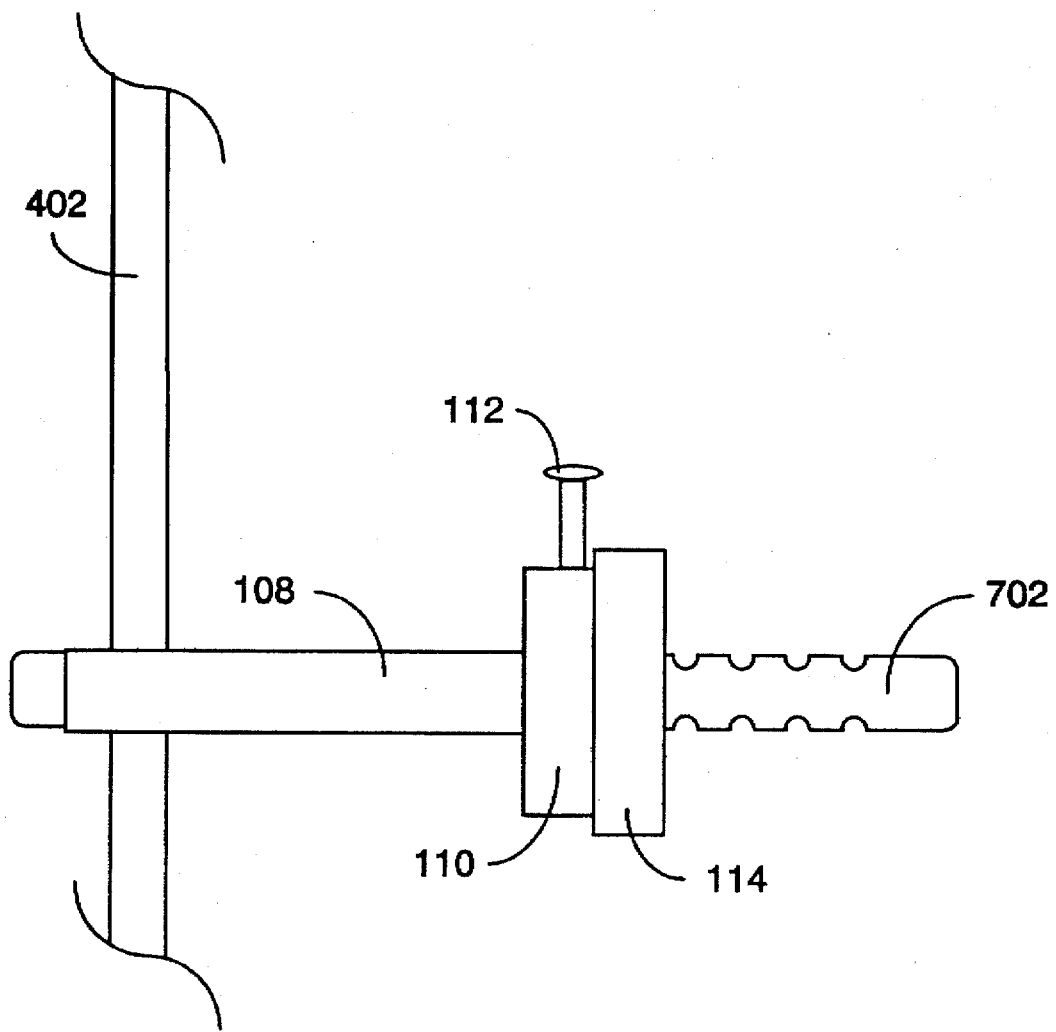
FIG. 9 illustrates the second guide rod inserted into the peritoneal cavity through the first cannula.

FIG. 9 shows guide rod 702 inserted into the peritoneal cavity via first cannula 108. The diameter of guide rod 702 is designed to snugly and slidably fit within the inside diameter of first cannula 108. Once guide rod 702 is inside the body cavity, first cannula 108 can be withdrawn over guide rod 702.

Figure 10:
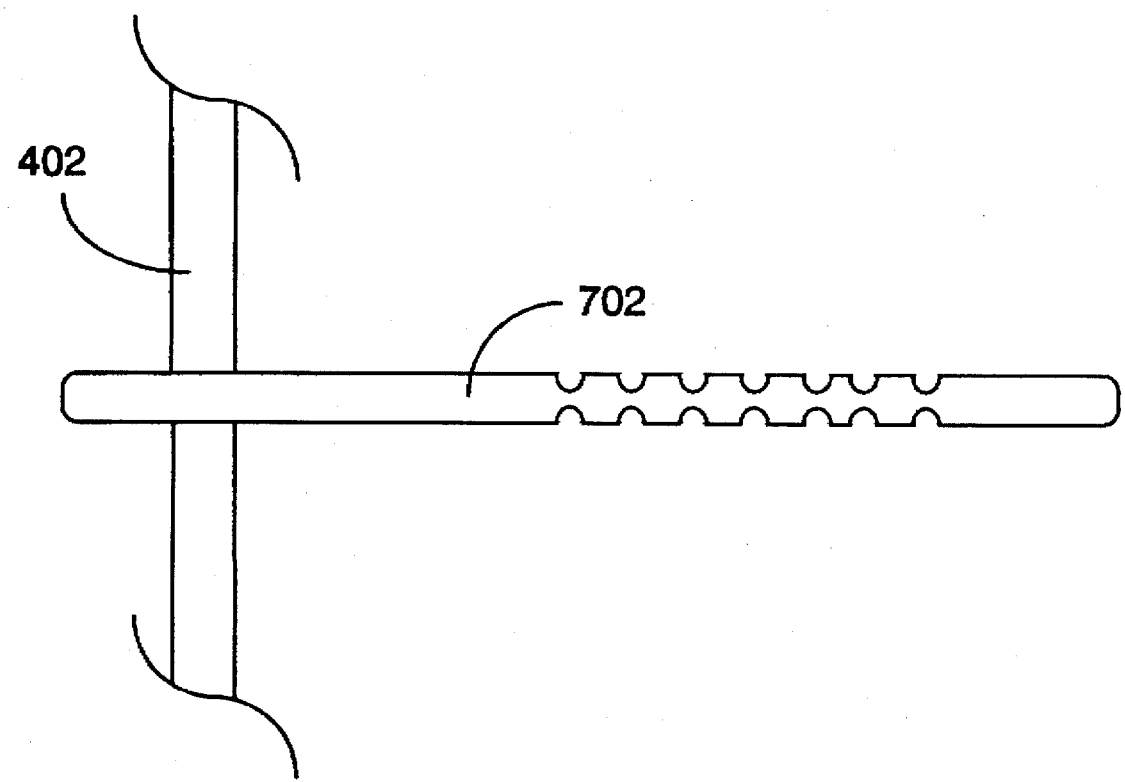
FIG. 10 illustrates the second guide rod inserted into the peritoneal cavity after the first cannula has been removed.

As shown in FIG. 10, when first cannula 108 is withdrawn, second guide rod 702, which is substantially the same diameter as first cannula 108, maintains the patency of opening in the peritoneal wall 402.

Figure 11:
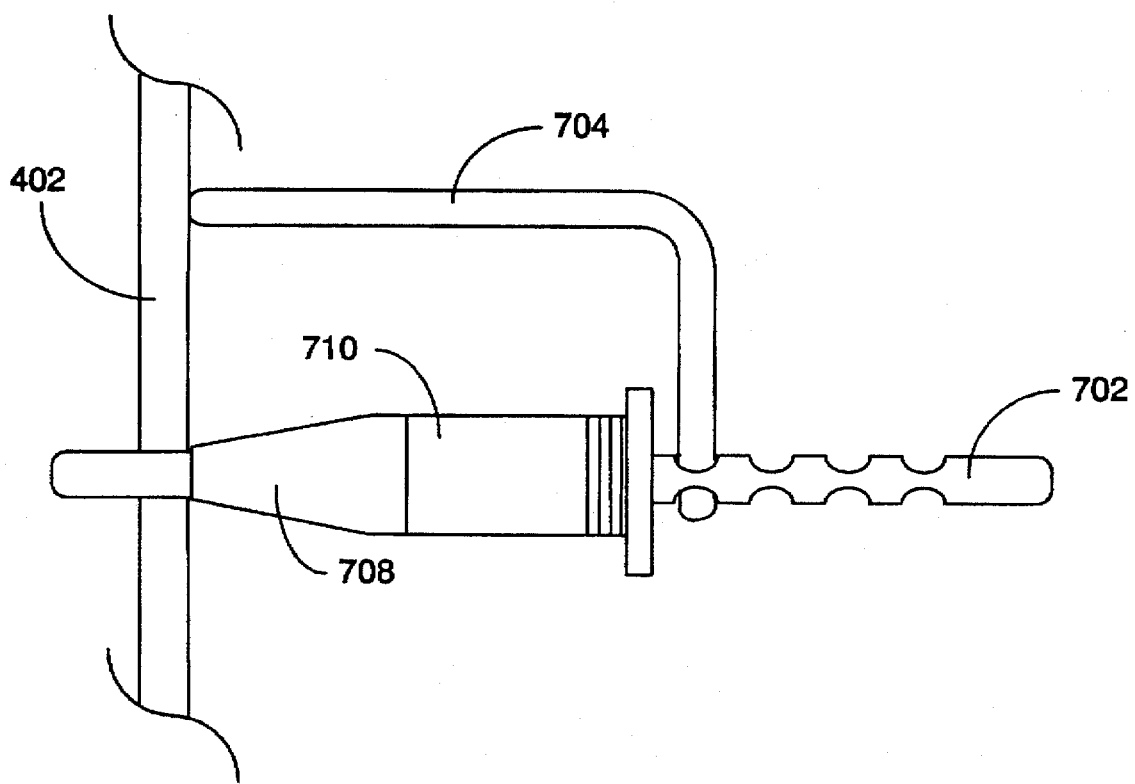
FIG. 11 illustrates the second blunt dilator before advancing it into the tissue track which is backloaded with a digital cannula. The second handle has been adjusted to touch the outside of the abdominal wall to stabilize the depth of the second guide rod in the peritoneal cavity.

FIG. 11 shows second dilator 708 and digital cannula 710 mounted on guide rod 702. In this position, second dilator 708 and digital cannula 710 are ready to slide forward into the peritoneal cavity. Prior to introducing the second dilator 708 and digital cannula 710 into the tissue track, the distal end of second handle 704 is attached and adjusted to be in close proximity to the abdominal wall surface such that guide rod 702 is prevented from excessively penetrating into the peritoneal cavity.

Figure 12:
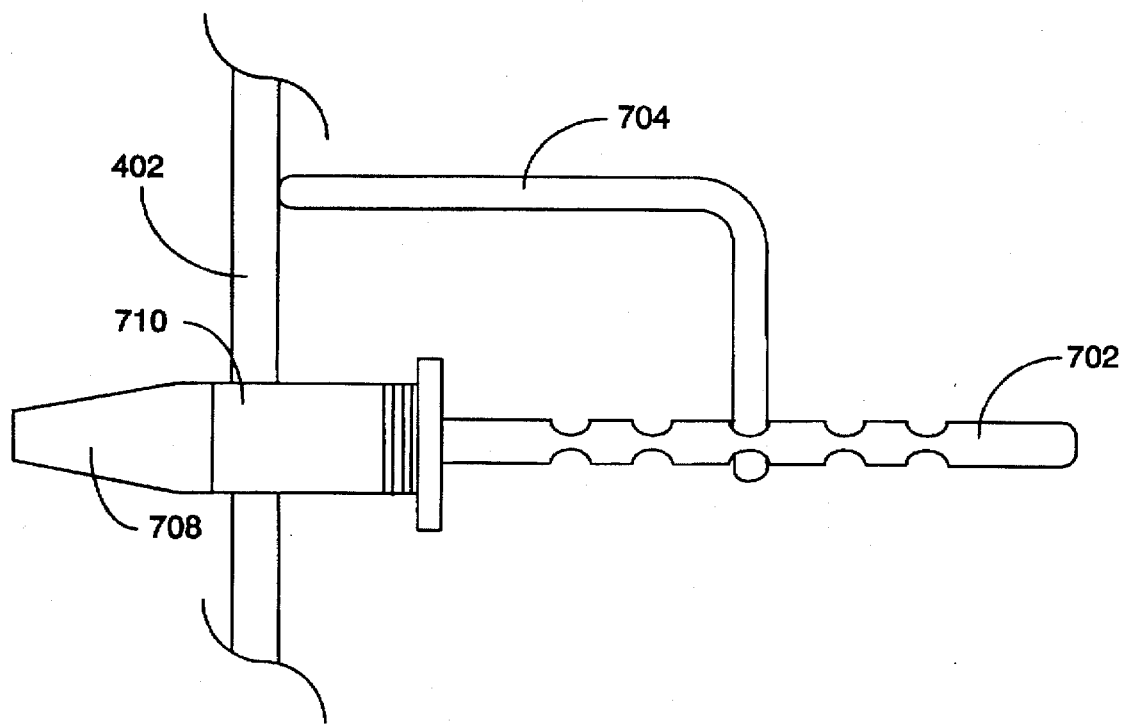
FIG. 12 shows the second dilator and digital cannula after they are introduced into the peritoneal cavity and advanced past the distal end of the guide rod which has been prevented from advancing by the handle.

In FIG. 12, second dilator 708 and the second cannula 710 have entered the peritoneal cavity. The position of the second guide rod 702 is maintained with handle 704.

Figure 13:
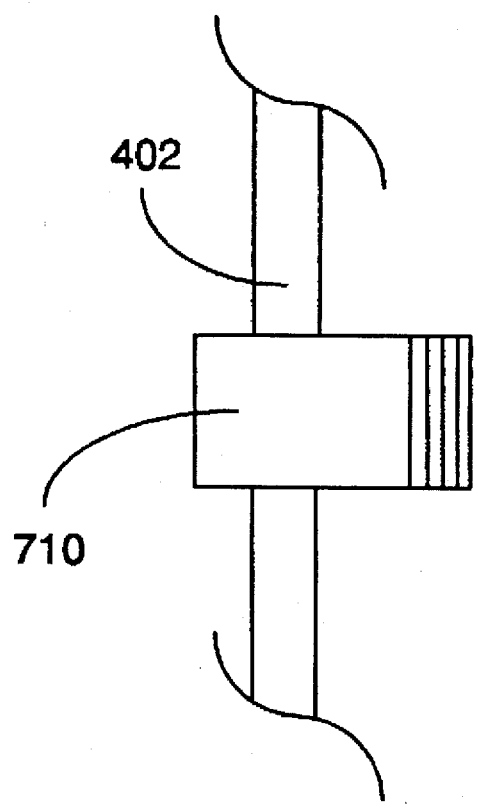
FIG. 13 illustrates the digital cannula inserted through the abdominal wall and after the second dilator has been removed. At this point the surgeon has the option to proceed laparoscopically either by attaching the seal ensemble for use with laparoscopic instruments or by sealing the peritoneal cavity with a digital seal that is attached over the proximal end of the digital cannula with an O-ring.

FIG. 13 illustrates the next step which is the removal of components other than digital cannula 710. In the preferred embodiment, the digital cannula 710 has an inside diameter sufficiently large to accommodate the surgeon's finger for dissection, palpation, and orientation. Of course, the increased size of digital cannula 710 allows other conveniences, such as the easy removal of tissue samples.

As can be seen, by progressively expanding the opening in the peritoneal wall 402 with increasingly larger dilators, a substantial opening can be created without having to use a trocar. The result is substantially reduced tissue damage for the patient.

Figure 14A:
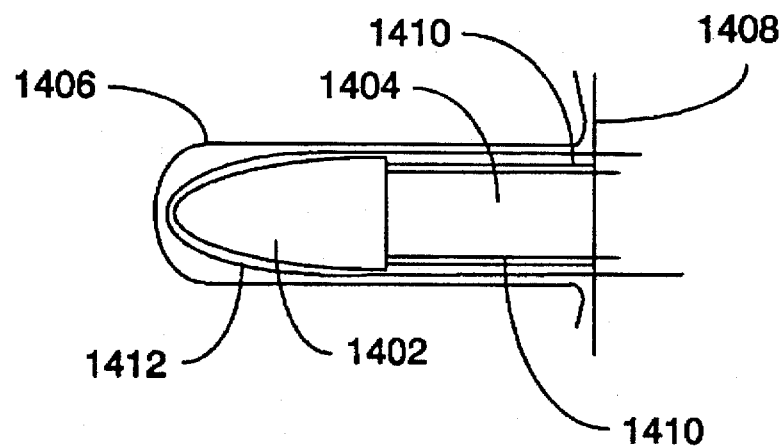
FIG. 14A illustrates an optional digital thimble mounted between first and second surgical gloves on the fingertip of the surgeon's finger. The digital cannula is sealed with a digital seal made from a flexible material such as a latex finger or condom. An O-ring is mounted on the surgeon's finger prior to insertion into the digital seal.

FIG. 14A illustrates a thimble 1402 which is held on the tip of a surgeon's finger 1404 by a second glove 1412. The surgeon's finger 1404 is inside a surgical glove 1410. Thimble 1402 is then mounted over it and held in place by a second glove 1412. Thimble 1402 increases the reach of the surgeon when manipulating the patient's tissue inside the body cavity and maintains tactile feedback and enhanced maneuverability.

Figure 14B:
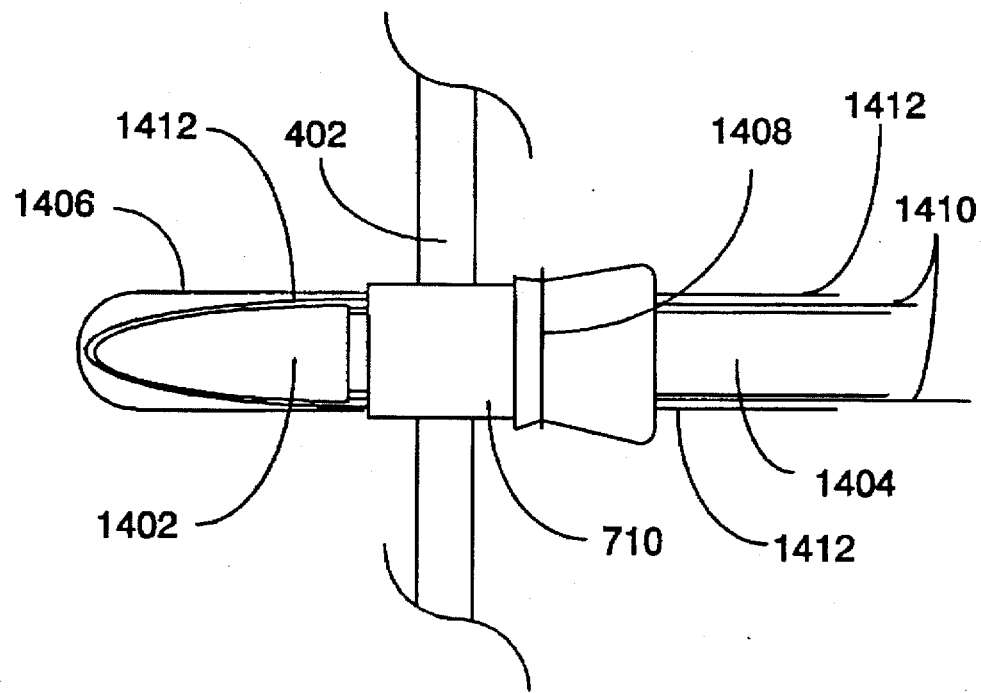
FIG. 14B illustrates the embodiment of FIG. 14A after the digital seal has been folded over the outside of the proximal end of the digital cannula and attached with the O-ring.

In FIG. 14B, digital seal 1406 is folded over the outside of digital cannula 710. Elastic band (or O-ring) 1408 is used to seal digital seal 1406 to digital cannula 710.

The digital seal 1406 can be implemented by using a suitable portion of a conventional latex glove; or using a finger sized sheath; or even as a simple device as a condom. The digital seal 1406 is folded over the outer sleeve of the digital cannula 710 as shown in FIG. 14B. Elastic band 1408 can be a rubber band, o-ring, etc.

The aforedescribed procedure allows the substitution of larger sized cannulas. For example, a 10 or 12 mm for an 8 mm, or a 23 mm for a 10 mm cannula. However, even larger cannulas may be inserted using a single blunt dilator over a needle guide. Alternatively, the digital cannula can be inserted through a small minilaparotomy incision.

FIGS. 15A, 15B and 15C illustrate the use of an alternative embodiment of cannula 108 to allow insertion of multiple instruments such as a grasping forceps and a loop ligature. As shown in FIG. 15C, a single surgical device can be inserted through each of the slits 1502 in seal 302. In this embodiment, seal 302 is formed as a gasket, but may in fact take any suitable form capable of sealing the opening in the cannula 108. Seal cap 114 is threaded onto threaded seal base 110 and holds seal 302 firmly in place. Those skilled in the art will recognize that the number of devices introduced by cannula 108 can vary based on the size of the devices, the number of slits on seal 302, and the size of cannula 108. Likewise, the seal cap 114 does not have to be attached via a threaded screw type design as shown in the preferred embodiment, but may be any suitable mechanism such as snap on, pressure fit, etc.

FIG. 15C shows a cross sectional view of the cannula 108, seal 302, threaded seal base 110, and seal cap 114. The central opening in the proximal end of seal cap 114 is smaller than the diameter of seal 302. Seal cap 114 is removably attached to the threaded seal base 110 which in turn is removably threaded over threaded cannula base 304 (shown in FIG. 3). While the preferred embodiment uses a thread attachment, any suitable method of coupling the seal cap 114 to seal base 110 can be used, such as twist cap, cam lever, etc. The seal 302 has at least one slit 1502 to allow easy entry of a surgical instrument while closing the body cavity to maintain the gas pressure which has been insufflated therein at pressures up to 20 mm of mercury. When the instrument is removed, the resiliency of seal 302 automatically closes the slit 1502, such that the air tight seal is maintained at all times even when the instrument is removed. Seal 302 may be made from any suitable elastomeric material, such as silicone, polyurethane, polypropylene, nylon, rubber, etc. In the preferred embodiment, seal 302 is made from silicone and the slit 1502 is preferably cut such that it forms a cross with one of the slits longer than the other.

While the invention has been described in terms of particular embodiments, those skilled in the art will recognize that more than two cannula sizes may be used to progressively increase the opening in the peritoneal wall. Likewise a single dilator 106 can be used to open an aperture in the body cavity wall sufficiently large enough to allow a digital cannula 710 to be inserted with a single dilator insertion. An advantage of the multi-cannula capability disclosed herein is that the surgeon can vary the size of the opening in the body cavity wall to suit a particular surgical procedure without having to resort to a second body cavity penetration.

In addition, the system has been illustrated with two handles 120, 704 for ease of discussion. However, those skilled in the art will recognize that a single handle can be implemented which can be interchanged for use when installing either cannula 108 or the digital cannula 710.

In addition, while the invention has been described in terms in terms of gauge 14 insuflation needle and outer sleeves guide, those skilled in the art will recognize that the larger needle (for example, a gauge 12 needle) might be used with an outer sleeve to accommodate a contact scope through the needle. Alternatively, the needle may be placed outside the sleeve, which in the rest position may be extended past the needle tip.

While the invention has been described with respect to a preferred embodiment thereof, it will be understood by those skilled in the art that various changes in detail may be made therein without departing from the spirit, scope, and teaching of the invention. For example, the material used to construct the device may be anything suitable for surgical use, the size and shape of the cannula, the type of needle retraction mechanism, etc., can vary. Accordingly, the invention herein disclosed is to be limited only as specified in the following claims.

I claim:

1. A coaxial dilator system for insertion of laparoscopic cannulas through a body cavity wall without a trocar, comprising:

a coaxial dilator, further comprising:
  a needle having a distal end and a proximal end, the needle sufficiently sharp to penetrate a body cavity wall;
  a blunt outer sleeve guide having a central channel with an inside diameter sized to slidably accept the needle, the blunt outer sleeve guide attached to the needle by inserting the needle inside the central channel, the blunt outer sleeve guide further attached to the needle such that the needle is capable of moving in a proximal direction in relation to the blunt outer sleeve guide such that the distal tip of the needle can be withdrawn into the central channel after the body cavity wall is penetrated;
  a first blunt dilator, the first blunt dilator having a central dilator channel with an inside diameter sized to slidably accept the sleeve guide, the first blunt dilator attached to the blunt outer sleeve guide by inserting the blunt outer sleeve guide inside the central dilator channel, the first blunt dilator capable of sliding distally in relation to the blunt outer sleeve guide such that the blunt outer sleeve guide can be withdrawn from the body cavity once the first blunt dilator has penetrated the body cavity wall; and a first cannula, the first cannula having a central cannula channel with an inside diameter sized to slidably accept the first blunt dilator, the first cannula attached to the first blunt dilator by inserting the first blunt dilator inside the central cannula channel, the first cannula capable of sliding distally in relation to the first blunt dilator such that the first blunt dilator can be withdrawn from the body cavity once the first cannula has penetrated the body cavity wall; and a handle, the handle attached to and offset from the coaxial dilator via handle offset, the distal end of the handle positioned to limit penetration of the body cavity by the coaxial dilator, and further, the handle is distally adjustable such that the amount of body cavity penetration by the blunt outer sleeve guide can be selectably controlled by varying the relative position of the distal tip of the handle in relation to the abdominal wall of a patient;

whereby a cannula can be inserted into a body cavity wall without a trocar.

2. A coaxial dilator system for insertion of laparoscopic cannulas through a body cavity wall without a trocar, comprising:

a coaxial dilator, further comprising:

a needle having a distal end and a proximal end, the needle sufficiently sharp to penetrate a body cavity wall;

a blunt outer sleeve guide having a central channel with an inside diameter sized to slidably accept the needle, the blunt outer sleeve guide attached to the needle by inserting the needle inside the central channel, the blunt outer sleeve guide further attached to the needle such that the needle is capable of moving in a proximal direction in relation to the blunt outer sleeve guide such that the distal tip of the needle can be withdrawn into the central channel after the body cavity wall is penetrated;

a first blunt dilator the first blunt dilator having a central dilator channel with an inside diameter sized to slidably accept the sleeve guide, the first blunt dilator attached to the blunt outer sleeve guide by inserting the blunt outer sleeve guide inside the central dilator channel, the first blunt dilator capable of sliding distally in relation to the blunt outer sleeve guide such that the blunt outer sleeve guide can be withdrawn from the body cavity once the first blunt dilator has penetrated the body cavity wall; and a first cannula, the first cannula having a central cannula channel with an inside diameter sized to slidably accept the first blunt dilator, the first cannula attached to the first blunt dilator by inserting the first blunt dilator inside the central cannula channel, the first cannula capable of sliding distally in relation to the first blunt dilator such that the first blunt dilator can be withdrawn from the body cavity once the first cannula has penetrated the body cavity wall;

a handle, the handle attached to and offset from the coaxial dilator via a handle offset, the distal end of the handle positioned to limit penetration of the body cavity by the coaxial dilator;

a guide rod, the guide rod having an outside diameter of a size sufficient to slidably fit within the inner diameter of the first cannula after the needle, the blunt outer sleeve guide, and the first blunt dilator are removed;

a second blunt dilator having an internal channel of a size sufficient to slidably fit over the guide rod; and a digital cannula having an internal diameter of a size sufficient to slidably fit over the second blunt dilator;

whereby a cannula can be inserted into a body cavity wall without a trocar.

3. A coaxial dilator system, as in claim 2, further comprising:

a second handle, the second handle attached to the guide rod such that the location of the distal end of the guide rod cart be varied in relation to the distal end of the handle;

whereby penetration depth of the guide rod into the body cavity can be selectably controlled.

4. A coaxial dilator system, as in claim 3, further comprising a digital cannula seal ensemble attached to the proximal end of the digital cannula.

5. A coaxial dilator system, as in claim 4, wherein:

the digital cannula has an internal diameter of sufficient size to accommodate a surgeon's finger; and a seal capable of maintaining the pneumoperitoneum while the surgeon's finger is inside the body cavity.

6. A coaxial dilator system, as in claim 5, further comprising:

a digital thimble, having means to accept the tip of a surgeon's finger;

a digital seal mounted over the digital thimble such that a finger can be inserted into the digital cannula and into the digital thimble; and the digital thimble and digital seal sized such that they can be inserted into the body cavity via the digital cannula;

whereby the surgeon can manipulate internal structures in the patient's body cavity via the digital cannula.

7. A coaxial dilator system, as in claim 6, further comprising means to secure the digital seal to the digital cannula such that the body cavity is sealed while the digital thimble is inserted into the body cavity through the digital cannula.

8. A method of inserting laparoscopic cannulas through body cavity walls, including the steps of:

penetrating a body cavity wall with a needle having a distal end and a proximal end such that an aperture is created in the body cavity wall;

inserting a blunt outer sleeve guide slidably mounted over the needle, through the aperture in the body cavity wall;

controlling penetration of the body cavity by the blunt outer sleeve guide with an adjustable handle which has a distal end and a proximal end and is offset from the blunt outer sleeve guide via a handle offset, and positioning the location of the distal end of the handle to limit penetration of the body cavity by the blunt outer sleeve guide;

using a first blunt dilator to expand the aperture in the body cavity wall a sufficient width such that a first cannula can be inserted into the aperture;

removing the first blunt dilator and needle;

inserting a guide rod having an outside diameter of a size sufficient to slidably fit within the inner diameter of the first cannula;

removing the first cannula;

mounting a second blunt dilator having an internal channel of a size sufficient to slidably fit over the guide rod;

sliding the second blunt dilator forward into the body cavity wall and expanding the aperture in the body cavity wall;

inserting a digital cannula having an internal diameter of a size sufficient to slidably fit over the second blunt dilator onto the second blunt dilator and pushing the digital cannula into the body cavity wall; and removing the second blunt dilator and guide rod;

whereby a digital cannula can be inserted into a body cavity wall with a blunt dilator.

9. A method, as in claim 8, including the further steps of:

inserting a finger thimble into a digital seal;

inserting a finger into the digital seal and into the finger thimble; and using the finger to insert the finger thimble and digital seal into the digital cannula.

10. A method, as in claim 9, including the further steps of:

folding the proximal end of the digital seal over the outside surface of the digital cannula; and securing the digital seal to the digital cannula with an elastic ring.

11. A method as in claim 8, including the further steps of:

using a gas insufflation port in the digital cannula to insufflate the peritoneum; and using a seal ensemble in the internal channel of the digital cannula to prevent gas pressure loss.

* * * * *